US007674456B2

(12) United States Patent
Wiseman et al.

(10) Patent No.: US 7,674,456 B2
(45) Date of Patent: Mar. 9, 2010

(54) BREAST CANCER CELL LINES AND USES THEREOF

(75) Inventors: Charles Wiseman, 756 Fairfield Cir., Pasadena, CA (US) 91106; Alex Kharazi, Los Angeles, CA (US)

(73) Assignee: Charles Wiseman, Los Angeles, CA (US)

( * ) Notice: Subject to any disclaimer, the term of this patent is extended or adjusted under 35 U.S.C. 154(b) by 1447 days.

(21) Appl. No.: 10/868,094

(22) Filed: Jun. 14, 2004

(65) Prior Publication Data

US 2005/0276822 A1 Dec. 15, 2005

(51) Int. Cl.
 *A61K 35/12* (2006.01)
(52) U.S. Cl. .................. 424/93.21; 424/93.7; 424/573
(58) Field of Classification Search ................. None
 See application file for complete search history.

(56) References Cited

U.S. PATENT DOCUMENTS

| | | | |
|---|---|---|---|
| 5,078,996 A | 1/1992 | Conlon et al. | |
| 5,286,642 A | 2/1994 | Doersen et al. | |
| 5,290,684 A | 3/1994 | Kelly et al. | |
| 5,436,152 A | 7/1995 | Soule et al. | |
| 5,443,954 A | 8/1995 | Reddel et al. | |
| 5,637,483 A | 6/1997 | Dranoff et al. | |
| 5,693,533 A | 12/1997 | Raney et al. | |
| 5,824,488 A | 10/1998 | Webber et al. | |
| 5,904,920 A | 5/1999 | Dranoff et al. | |
| 6,037,520 A | 3/2000 | Raney et al. | |
| 6,082,364 A | 7/2000 | Balian et al. | |
| 6,284,537 B1 | 9/2001 | Offord Cavin et al. | |
| 6,350,445 B1 | 2/2002 | Jaffee et al. | |
| 6,403,104 B1 | 6/2002 | Berd | |
| 6,541,249 B2 | 4/2003 | Wager et al. | |
| 7,256,037 B2 * | 8/2007 | Ellenhorn et al. ........ 435/320.1 |
| 7,271,156 B2 * | 9/2007 | Krieg et al. .................... 514/44 |
| 2002/0006413 A1 | 1/2002 | Sobol et al. | |
| 2002/0039571 A1 | 4/2002 | Falkenberg et al. | |
| 2002/0085997 A1 | 7/2002 | Schmidt et al. | |
| 2002/0182194 A1 | 12/2002 | Ju et al. | |
| 2003/0003088 A1 | 1/2003 | Tsao et al. | |
| 2003/0124103 A1 | 7/2003 | Ostrand-Rosenberg et al. | |
| 2003/0129206 A1 | 7/2003 | Ulbrich et al. | |
| 2003/0170756 A1 | 9/2003 | Berd et al. | |
| 2003/0228300 A1 | 12/2003 | Haspel et al. | |
| 2004/0071739 A1 | 4/2004 | Green et al. | |

FOREIGN PATENT DOCUMENTS

| | | | |
|---|---|---|---|
| WO | WO 97/00085 | | 1/1997 |
| WO | WO00/20027 | * | 4/2000 |
| WO | WO 00/72686 | | 12/2000 |

OTHER PUBLICATIONS

NML Gateway MeSH Term Information, downloaded Dec. 30, 2008.*

Liu et al, Biochemistry, 1995, vol. 34, pp. 10474-10482.*
Park et al, Proceeding of the National Academy of Science, 1995, vol. 92, pp. 1327-1331.*
Gatenby et al, Cancer Research, 2002, vol. 62, pp. 3675-3684.*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Tolcher et al (Clinical Cancer Research, 2002, vol. 8, pp. 2530-2535).*
Cripps et al (Clinical Cancer Research. 2002, 8, pp. 2188-2192).*
Gazdar et al (International Journal of Cancer, 1998, vol. 78, pp. 766-744).*
Guo et al (Nature Medicine, 1997, vol. 3, pp. 451-455).*
Vogel et al (The Breast Journal, 2003, vol. 9, pp. 452-462).*
Dols A et al., "Allogeneic Breast Cancer Cell Vaccines", Clinical Breast Cancer, vol. 3, No. 4, pp. S173-S180 (2003).
Baars A et al., "Making Use of the Primary Tumour", Bioessays, Cambridge, GB, vol. 25, No. 1, pp. 79-86 (2002).
Chapman, Paul, "Vaccinating Patients With Autologous Tumor", Journal of Clinical Oncology, vol. 20, No. 20, pp. 4139-4140, Oct. 15, 2002.
Shinohara, H. et al., "Induction of Chemokine Secretion and Enhancement of Contact-Dependent Macrophage Cytotoxicity by Engineered Expression of Granulocyte-Macrophage Colony-Stimulating Factor in Human Colon Cancer Cells", Journal of Immunology, 164: 2728-2737, 2000.
Machiels, J. et al., Cyclophosphamide, Doxorubicin, and Paclitaxel Enhance the Antitumor Immune Response of Granulocyte/Macrophage-Colony Stimulating Factor-secreting Whole-Cell Vaccines in HER-2/*neu* Tolerized Mice, Cancer Research, 61, pp. 3689-3697, May 1, 2001.
Dranoff, G. et al., "Vaccination with irradiated tumor cells engineered to secrete murine granulocyte-macrophage colony-stimulating factor stimulates potent, specific, and long-lasting anti-tumor immunity", Proc. Natl. Acad. Sci. USA, vol. 90, pp. 3539-3543, Apr. 1993.
Soiffer, R. et al., "Vaccination with irradiated autologous melanoma cells engineered to secrete human granulocyte-macrophage colony-stimulating factor generates potent antitumor immunity in patients with metastatic melanoma", Proc. Natl. Acad. Sci. USA, vol. 95, pp. 13141-13146, Oct. 1998.
Jaffee, E. et al., "Novel Allogeneic Granulocyte-Macrophage Colony-Stimulating Factor-Secreting Tumor Vaccine for Pancreatic Cancer: A Phase I Trial of Safety and Immune Activation", Journal of Clinical Oncology, vol. 19, No. 1, pp. 145-156, Jan. 1, 2001.

(Continued)

*Primary Examiner*—Karen A Canella
(74) *Attorney, Agent, or Firm*—Karen S. Canady; canady + lortz LLP

(57) ABSTRACT

The invention provides, in part, novel SV-BR cancer cell lines. The invention provides a novel cell line SV-BR-1 deposited under ATCC PTA-1712 and SV-BR-1-GM cells deposited under ATCC PTA-1713. The invention further relates to therapeutic and non-therapeutic uses of the novel cell lines. Therapeutic uses include the use of SV-BR cell lines as cancer vaccines, and in particular, or the treatment of cancer.

40 Claims, 2 Drawing Sheets

OTHER PUBLICATIONS

Dols, A. et al., "Vaccination of Women with Metastatic Breast Cancer, Using a Costimulatory Gene (CD80)-Modified, HLA-A2-Matched, Allogeneic, Breast Cancer Cell Line: Clinical and Immunological Results", Human Gene Therapy 14:1117-1123, Jul. 20, 2003.

Jiang, X. et al., Vaccination with a Mixed Vaccine of Autogenous and Allogeneic Breast Cancer Cells and Tumor Associated Antigens CA15-3, CEA and CA125-Results in Immune and Clinical Responses in Breast Cancer Patients, Cancer Biotherapy & Radiopharmaceuticals, vol. 15, No. 5, pp. 495-505, 2000.

Nemunaitis, J. et al., "Granulocyte-Macrophage Colony-Stimulating Factor Gene-Modified Autologous Tumor Vaccines in Non-Small-Cell Lung Cancer", Journal of the National Cancer Institute, vol. 96, No. 4, pp. 326-331.

Emens, L. et al., "A Phase I Vaccine Safety and Chemotherapy Dose-Finding Trial of an Allogeneic GM-CSF-Secreting Breast Cancer Vaccine Given in a Specifically Time Sequence with Immunomodulatory Doses of Cyclophosphamide and Doxorubicin", Human Gene Therapy, 15:313-337, Mar. 2004.

* cited by examiner

BREAST CANCER CELL LINES AND USES THEREOF

BACKGROUND OF THE INVENTION

Cancer is considered to be a serious and pervasive disease. The National Cancer Institute has estimated that in the United States alone, 1 in 3 people will be afflicted with cancer during their lifetime. Moreover approximately 50% to 60% of people contracting cancer will eventually die from the disease.

One particularly prevalent form of cancer, especially among women, is breast cancer. The incidence of breast cancer, a leading cause of death in women, has been gradually increasing in the United States over the last thirty years. In 1997, it was estimated that 181,000 new cases were reported in the U.S., and that 44,000 people would die of breast cancer (Parker et al, 1997, *CA Cancer J. Clin.* 47:5-27; Chu et al, 1996, *J. Nat. Cancer Inst.* 88:1571-1579). Similarly, lung cancer is the second most common cause of cancer and the leading cause of cancer deaths for both men and women in the United States, with an estimated 171,000 new cases in 2003. The five-year survival rate among all lung cancer patients, regardless of the stage of disease at diagnosis, is only 13%.

In 2003, about 25,400 new cases of ovarian cancer were diagnosed according to estimates from the American Cancer Society (ACS). Among U.S. women, ovarian cancer is the seventh most common cancer and the fifth leading cause of cancer death after lung and bronchus, breast, colorectal, and pancreatic cancers. The ACS also estimated that there were approximately 105,500 new cases of colon cancer and 42,000 new cases of rectal cancer in 2003 in the United States.

In spite of considerable research into therapies, these and other cancers remain difficult to diagnose and treat effectively. Accordingly, there is a need in the art for improved methods for detecting and treating such cancers. The present invention fulfills these needs and further provides novel cell lines and compositions comprising said cell lines.

SUMMARY OF THE INVENTION

The application provides compositions comprising at least one SV-BR cancer cell, wherein an SV-BR cancer cell has at least two of the following characteristics: (a) grows as an epithelial, adherent monolayer culture; (b) does not overexpress estrogen receptors; (c) overexpresses her2/neu; (d) is sensitive in vitro to cyclophosphamide (4HC): (e) is sensitive in vitro to etoposide; (f) is sensitive in vitro to taxol; (g) is resistant in vitro to carboplatin; (h) demonstrates karyotypic abnormalities such as at least one of the following: 57-60, XX+1, add(1)(36.3), del(1)add(1)(p36.3)add(1)(q32), i(3)(q10), add(4)(p16), +6, −10, −10, +11, +12, −14, +15, +16, add(19)(q13.4), +20, −21, −21, +11 −13mar[cp20]; and (i) is aneuploid In one aspect, the cell is a mammalian cancer cell, such as for example, a breast cancer cell, an ovarian cancer cell or a lung cancer cell. In one embodiment, the cell is a human cancer cell, such as for example a breast cancer cell, an ovarian cancer cell, or a lung cancer cell. In one embodiment, the composition comprises an SV-BR-1 cell, deposited as American Type Culture Collection (ATCC) Accession No. PTA-1712, or an SV-BR-1-GM cell, deposited as American Type Culture Collection Accession No. PTA-1713, both of which deposits were received by ATCC, 10801 University Blvd., Manassas, Va. 20110-2209 USA, on Aug. 16, 2006.

The invention also provides compositions comprising at least one SV-BR cell and a physiologically acceptable carrier, such as compositions for inducing an immune response in a subject in need thereof. The invention also provides methods of using SV-BR cells, such as but not limited to using SV-BR-1 and SV-BR-1-GM cells, for therapeutic applications, and in particular as in cancer vaccines. One aspect of the invention provides a method of inducing an immune response in a subject in need thereof, comprising administering to the subject a therapeutically effective amount of a composition comprising at least one SV-BR cell. A related aspect of the invention provides a method of treating a tumor in a subject in need thereof, comprising administering to the subject a therapeutically effective amount of a composition comprising an SV-BR cell. A related aspect of the invention provides tumor vaccines which ameliorate at least one symptom of cancer in a subject. In some embodiments, the cancer is one in which the cancer cells overexpress her2, such as but not limited to breast, ovarian or lung cancer.

The invention further provides SV-BR cell lines, such as SV-BR-1 or SV-BR-1-GM cell lines, for the manufacture of medicaments to treat diseases. Any methods disclosed herein for generating an immune response or for the treatment of cancer which comprise administering SV-BR cells to a subject may be applied to the use of the cells in the manufacture of a medicament to generate the immune response or treat cancer. Accordingly, one aspect of the invention provides the use of SV-BR-1 or SV-BR-1-GM cells for the manufacture of a medicament for inducing an immune response or for treating cancer in a subject in need thereof. In one preferred embodiment, the cancer is breast, ovarian, lung cancer. In other embodiments, adjuvants, antineoplastic agents, immunomodulatory agents, cancer antigens, chemotherapeutics and the like may also be used in the manufacture of said medicament.

While the present invention is described herein with reference to the particular cell lines disclosed e.g. SV-BR-1 and SV-BR-1-GM, it should nevertheless be understood to those skilled in the art that the present invention contemplates SV-BR cells as described herein.

DETAILED DESCRIPTION OF THE INVENTION

I. Overview

Figure 1:
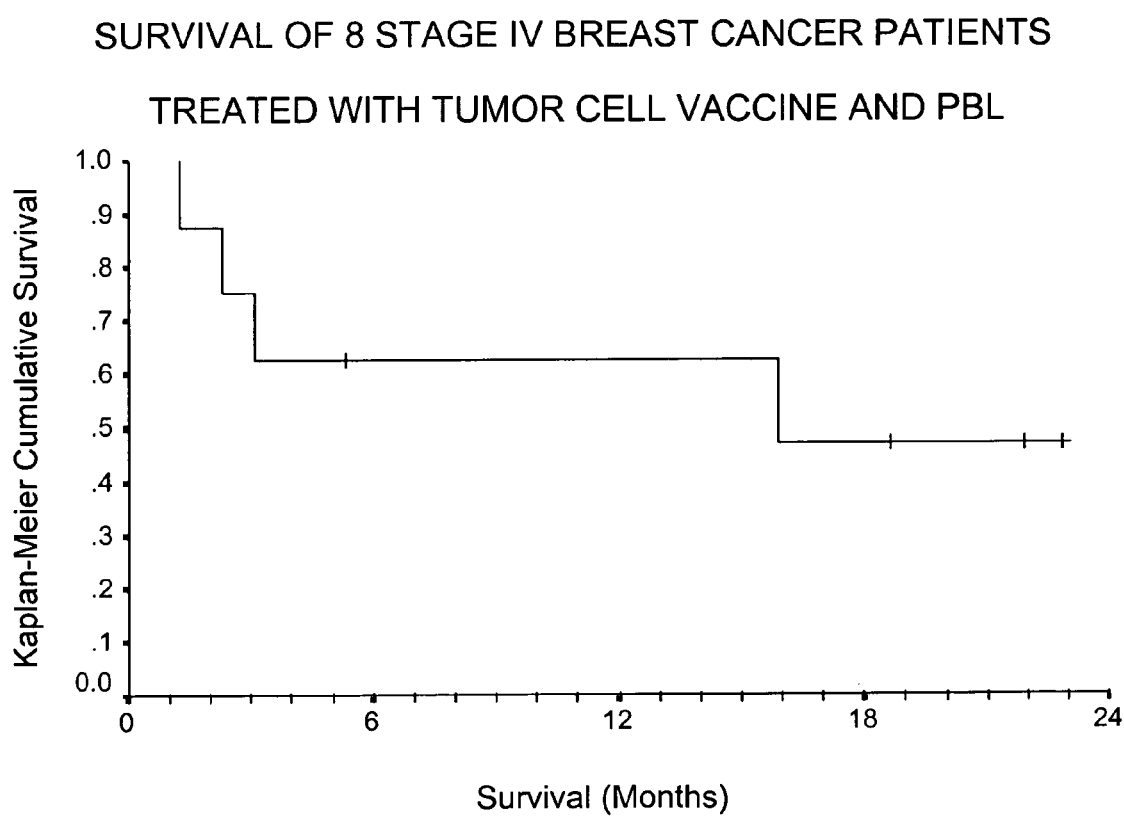
FIG. 1 depicts the survival rates of eight stage IV breast cancer patients treated with an SV-BR-1 tumor vaccine.

The invention broadly relates to novel cell lines and uses thereof. One aspect of the invention relates to SV-BR cells and cell lines. The invention further relates to methods of using SV-BR cells, such as their use as tumor vaccines to treat the symptoms of cancer or to elicit an immune response in a subject in need thereof.

One aspect of the invention provides a composition comprising at least one SV-BR cell. An SV-BR cell is a cancer cell having at least two of the following characteristics: (a) grows as an epithelial, adherent monolayer culture; (b) does not overexpress estrogen receptors; (c) overexpresses her2/neu; (d) is sensitive in vitro to cyclophosphamide (4HC); (e) is sensitive in vitro to etoposide; (f) is sensitive in vitro to taxol; (g) is resistant in vitro to carboplatin; (h) demonstrates karyotypic abnormalities such as 57-60, XX+1, add(1)(36.3), del (1)add(1)(p36.3)add(1)(q32), i(3)(q10), add(4)(p16), +6, −10, −10, +11, +12, −14, +15, +16, add(19)(q13.4), +20, −21, −21, +11 −13mar[cp20]; (i) is aneuploid. In one embodiment, the SV-BR cancer cell is a cancer cell having at least three, four, five, six, seven, eight or nine of these characteristics. In one embodiment, the SV-BR cell is a breast, colon, lung or ovary cell.

A related aspect of the invention provides a composition comprising at least one SV-BR-1 cell, deposited as American Type Culture Collection Accession No. PTA-1712. Another related aspect provides a composition comprising at least one SV-BR-1-GM cell, deposited as American Type Culture Collection Accession No. PTA-1713.

Another aspect of the invention provides a composition for inducing an immune response in a subject in need thereof, comprising (a) at least one SV-BR cell and (b) a physiologically acceptable carrier. A related aspect of the invention provides a composition for inducing an immune response in a subject in need thereof, comprising (a) at least one SV-BR-1 cell, deposited as American Type Culture Collection Accession No. PTA-1712; and (b) a physiologically acceptable carrier. Another related aspect of the invention provides a composition for inducing an immune response in a subject in need thereof, comprising (a) at least one SV-BR-1-GM cell, deposited as American Type Culture Collection Accession No. PTA-1713; and (b) a physiologically acceptable carrier. In one embodiment, the immune response comprises a Th1 response. In a specific embodiment, the immune response comprises an immune response against a subject's tumor cell.

In other embodiments, the application provides compositions comprising at least one SV-BR cell, wherein said cell has been further modified to express at least one polypeptide. In a specific embodiment, the polypeptide is selected from the group consisting of a chemokine, a cytokine, a growth factor, a tumor antigen or an antibody. Growth factors include Flt3L polypeptides, while tumor antigens include HER2/neu, CA15.3, CD31, CD105, Tie-2/Tek, NY-ESO-1, MTA1, MUC1, (CEA), Ep-CAM, p53, MAGE 1, 2, 3, 4, 6 or 12, and Thompson-Friedenreich antigen. Cytokines include but are not limited to IFN-α, IL-2, IL-4, IL-12 and GM-CSF. In other embodiments, the antibody comprises a monoclonal antibody, a humanized antibody, a single chain antibody or a chimeric antibody. In a preferred embodiment, the antibody is specific for a cancer antigen, such as for example a breast cancer antigen, an ovarian cancer antigen, or a lung cancer antigen.

In one embodiment, the application provides compositions comprising an SV-BR cell, wherein said SV-BR cell has been further modified to express a cytokine such as IFN-alpha, IL-2, IL-4, IL-12 and GM-CSF. In a specific embodiment, the application provides compositions comprising an SV-BR cell modified to express GM-CSF, such as SV-BR-1-GM, deposited as American Type Culture Collection Accession No. PTA-1713.

In yet another embodiment, the composition comprises cells that are irradiated cells, cells treated with a crosslinking agent, or cells treated with an agent which inhibits proliferation of the tumor cells in the subject. In embodiments of the compositions described herein, the SV-BR cell is an SV-BR-1 or an SV-BR-GM cell. Accordingly, the invention also provides compositions comprising at least one SV-BR-1 cell or at least one SV-BR-1-GM cell.

Another aspect of the invention provides a method of inducing an immune response in a subject in need thereof, comprising administering to the subject a therapeutically effective amount of a composition comprising at least one SV-BR cell. A related aspect of the invention provides a method of treating a tumor or a cancer in a subject in need thereof, comprising administering to the subject a therapeutically effective amount of a composition comprising at least one SV-BR cell. In some embodiments of the methods described herein, the SV-BR cell is an SV-BR-1 cell or an SV-BR-1-GM cell. In some embodiments, the compositions ameliorate the symptoms of cancer. In another embodiment, the compositions prophylactically treat the symptoms of cancer. In another embodiment, the composition is administered to the subject at least twice.

In some embodiments of the methods described herein, the subject in need thereof is afflicted with a tumor or with cancer, such as breast cancer, the breast cancer may be a stage 0, I, II, III or IV stage breast cancer. The breast cancer may comprise a ductal carcinoma or a lobular carcinoma. In another embodiment, the cancer is one where the cancer cells overexpress her2 or EGFR or both, or any other cancer antigen that is overexpressed in SV-BR-1 cells. In another embodiment, the cancer is an ovarian or lung cancer.

In some embodiments of the compositions and methods for inducing an immune response in a subject in need thereof, the subject is afflicted with a tumor or with cancer, such as breast cancer, ovarian cancer or lung cancer. In embodiments where the cancer is breast cancer, the cancer may comprise a ductal hyperplasia, a carcinoma in situ, an invasive ductal carcinoma, or a combination thereof. In some embodiments, the subject has undergone or is undergoing surgery, chemotherapy, radiation therapy, hormonal therapy or a combination thereof, at the time that the methods of treatment described herein are applied. In a specific embodiment, the subject is a chemotherapy subject.

In another embodiment of the compositions and methods described herein, the compositions comprise additional cells of a second type, such as a lymphocyte or another type of tumor cell. In a specific embodiment, the composition further comprises autologous cells. The autologous cells may comprise a macrophage, a dendrite, a monocyte or a T cell, or a tumor cell. In specific embodiments, the autologous cell has been contacted with an antigen, such as a cancer antigen.

The compositions of the methods described herein may comprise additional agents, such as adjuvants or antineoplastic agents. Antineoplastic agents include but are not limited to, RNAi reagents, tumor cells and antibodies. In a specific embodiment, the antineoplastic agent is 5-Fluoruracil, 6-mercatopurine, Actinomycin, Adriamycin®, Adrucil®, Aminoglutethimide, Anastrozole, Aredia®, Arimidex®, Aromasin®, Bonefos®, Bleomycin, carboplatin, Cactinomycin, Capecitabine, Cisplatin, Clodronate, Cyclophosphamide, Cytadren®, Cytoxan®, Dactinomycin, Docetaxel, Doxorubicin, Epirubicin, Etoposide, Exemestane, Femara®, Fluorouracil, Fluoxymesterone, Halotestin®, Herceptin®, Letrozole, Leucovorin calcium, Megace®, Megestrol acetate, Methotrexate, Mitomycin, Mitoxantrone, Mutamycin®, Navelbineg, Nolvadex®, Novantrone®, Oncovin®, Ostac®, Paclitaxel, Pamidronate, Pharmorubicin®, Platinol®, prednisone, Procytox®, Tamofen®, Tamone®, Tamoplex®, Tamoxifen, Taxol®, Taxotere®, Trastuzumab, Thiotepa, Velbe®, Vepesid®, Vinblastine, Vincristine, Vinorelbine or Xeloda®.

In some embodiments, the compositions comprise an immunomodulatory agents, such as cytokines. Cytokines include IFN-α, IL-2, IL-4, IL-12 and GM-CSF. In another embodiment, the composition further comprises an immunomodulatory drug, such as cyclophosphamide. In other embodiments, the compositions comprise adjuvants.

In another embodiment, the antineoplastic agent is an antibody selected from the group consisting of RITUXAN™ (rituximab), IDEC-C2B8, anti-CD20 Mab, PANOREX™ (edrecolomab), 3622 W94, anti-EGP40 (17-1A) pancarcinoma antigen on adenocarcinomas, Herceptin, Erbitux, anti- Her2, Anti-EGFr, BEC2, anti-idiotypic-GD₃ epitope. Ovarex. B43.13, anti-idiotypic CA125, 4B5. Anti-VEGF. RhuMAb. MDX-210, anti-HER2. MDX-22, MDX-220, MDX-447, MDX-260, anti-GD-2, QUADRAMET™ (samarium SM 153 Lexidronam), CYT-424, IDEC-Y2B8, ONCOLYM™, Lym-1, SMART™ 195. ATRAGEN™ (all-trans retinoic acid—ATRA), LDP-03, anti-CAMPATH, anti CD6, MDX-11, OV103, Zenapax, Anti-Tac, anti-IL-2 receptor. MELIMMIJNE™-2, MELIMMUNE™-1, CEACIDE™ (antibody to carcinoembryonic antigen), PRETARGET™ (anti-CD20 fusion protein), NovoMAb-G2, TNT, anti-histone, Gliomab-H, GNI-250, EMD-72000, LYMPHOCIDE™ (Epratuzumab), CMA 676, Monopharm-C, anti-FLK-2, SMART™ ID10, SMART™ ABL 364, and ImmuRAIT-CEA.

II. Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

A "patient" or "subject" to be treated by the method of the invention can mean either a human or non-human animal, preferably a mammal.

The term "expression vector" and equivalent terms are used herein to mean a vector which is capable of inducing the expression of DNA that has been cloned into it after transformation into a host cell. The cloned DNA is usually placed under the control of (i.e., operably linked to) certain regulatory sequences such a promoters or enhancers. Promoters sequences maybe constitutive, inducible or repressible.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

The term "recombinant" is used herein to mean any nucleic acid comprising sequences which are not adjacent in nature. A recombinant nucleic acid may be generated in vitro, for example by using the methods of molecular biology, or in vivo, for example by insertion of a nucleic acid at a novel chromosomal location by homologous or non-homologous recombination.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

The term "prophylactic" or "therapeutic" treatment refers to administration to the subject of one or more of the subject compositions. If it is administered prior to clinical manifestation of the unwanted condition (e.g., cancer or the metastasis of cancer) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain cell lines of the present invention may be administered in a sufficient amount to produce a reasonable benefit/risk ratio applicable to such treatment.

The term "effective amount" refers to the amount of a therapeutic reagent that when administered to a subject by an appropriate dose and regimen produces the desired result.

The term "subject in need of treatment for a disorder" is a subject diagnosed with that disorder or suspected of having that disorder.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies.

The term "antineoplastic agent" is used herein to refer to agents that have the functional property of inhibiting a development or progression of a neoplasm or neoplastic cell growth in a human, particularly a malignant (cancerous) lesion, such as a carcinoma, sarcoma, lymphoma, or leukemia.

The terms "overexpressed" or "underexpressed" typically relate to expression of a nucleic acid sequence or protein in a cancer cell at a higher or lower level, respectively, than that level typically observed in a non-tumor cell (i.e., normal control). In preferred embodiments, the level of expression of a nucleic acid or a protein that is overexpressed in the cancer cell is at least 10%, 20%, 40%, 60%, 80%, 100%, 200%, 400%, 500%, 750%, 1,000%, 2,000%, 5,000%, or 10,000% greater in the cancer cell relative to a normal control.

The term "sensitive to a drug" or "resistant to a drug" is used herein to refer to the response of a cell when contacted with an agent. A cancer cell is said to be sensitive to a drug when the drug inhibits the cell growth or proliferation of the cell to a greater degree than is expected for an appropriate control, such as an average of other cancer cells that have been matched by suitable criteria, including but not limited to, tissue type, doubling rate or metastatic potential. In some embodiments, greater degree refers to at least 10%, 20%, 30%, 40%, 50%, 60%, 70%, 80%, 90%, 100%, 200%, or 500%. A cancer cell is said to be sensitive to a drug when the drug inhibits the cell growth or proliferation of the cell to a lesser degree than is expected for an appropriate control, such as an average of other cancer cells that have been matched by suitable criteria, including but not limited to, tissue type, doubling rate or metastatic potential. In some embodiments, lesser degree refers to at least 10%, 15%, 20%, 25%, 50% or 100% less.

III. Compositions and Cell Lines

The invention provides compositions comprising at least one cancer cell. One aspect of the invention provides a composition comprising at least one SV-BR cell, wherein an SV-BR cell is a cell having at least two of the following characteristics: (a) grows as an epithelial, adherent monolayer culture; (b) does not overexpress estrogen receptors; (c) overexpresses her2/neu; (d) is sensitive in vitro to cyclophosphamide (4HC); (e) is sensitive in vitro to etoposide; (f) is sensitive in vitro to taxol; (g) is resistant in vitro to carboplatin; (h) demonstrates karyotypic abnormalities such as 57-60, XX+1, add(1)(36.3), del (1)add(1)(p36.3)add(1)(q32), i(3)(q10), add(4)(p16), +6, −10, −10, +11, +12, −14, +15, +16, add(19) (q13.4), +20, −21, −21, +11 −13mar [cp20]; (i) is aneuploid. In one embodiment, the SV-BR cancer cell is a cancer cell having at least three, four, five, six, seven, eight or nine of these characteristics. In one aspect, the SV-BR cell is a mammalian cancer cell, such as for example, a breast cancer cell, an ovarian cancer cell or a lung cancer cell. In one embodiment, the SV-BR is a human cancer cell, such as for example a breast cancer cell, an ovarian cancer cell, or a lung cancer cell.

In addition, SV-BR cells may have extensive chromosomal rearrangements. One skilled in the art would recognize that chromosomal rearrangements accumulate over time in immortalized cells as they are cultured in vitro, and thus the profile of such rearrangements in a cell population may vary over time. Analysis of chromosomal rearrangements in SV-BR-1 cells approximately two years prior to the filing of this application indicated the following representative karyotype abnormalities: 57-60, XX+1, add(1)(36.3), del (1)add(1)(p36.3)add(1)(q32), i(3)(q10), add(4)(p16), +6, −10, −10, +11, +12, −14, +15, +16, add(19) (q13.4), +20, −21, −21, +11 −13mar[cp20]. Such karyotype reflects structural abnormalities involving chromosomes 1, 3, 4, 6, 10, 11, 12, 14, 15, 16, 19, 20 and 21.

In some embodiments of the compositions and methods described herein, the SV-BR cell is genetically modified to express at least one polypeptide. In a specific embodiment, the polypeptide is selected from the group consisting of a chemokine, a cytokine, a growth factor, a tumor antigen, a T cell costimulatory molecule or an antibody. Methods of genetically engineering a cell to express a particular gene is well known to those skilled in the art (see Examples and Sambrook et al., Molecular Cloning: A Laboratory Manual, 2nd ed., Cold Spring Harbor Press, Plainview, N.Y. (1989); Ausubel et al., Current Protocols in Molecular Biology (Supplement 47), John Wiley & Sons, New York (1999)).

In another embodiment of the compositions and methods described herein, the SV-BR cells are genetically modified to inhibit the expression of an immunosuppressive agent, such as is described in U.S. Patent Publication No. 2002/0192199. As used herein, the term "immunosuppressive agent" refers to a gene product that has an inhibitory effect on the functions of the immune response. An immunosuppressive agent can interfere, for example, with the function of a cytokine or can inhibit or suppress the immune response by other mechanisms. Immunosuppressive agents are known in the art and include, for example, TGFβ, lymphocyte blastogenesis inhibitory factor, the retroviral p15E protein, suppressive E-receptor and extracellular matrix molecules such as fibronectin and tenascin (Olt et al., Cancer 70:2137-2142 (1992); Hemasath et al., J. Immunol. 152:5199-5207 (1994), each of which is incorporated herein by reference).

In one embodiment of the compositions and methods described herein, the SV-BR cell is transfected with a nucleic acid encoding a T cell costimulatory molecule in a form suitable for expression of the costimulatory molecule. The T cell costimulatory molecule may be a CD28 and/or CTLA4 ligand, such as a B lymphocyte antigen, B7.1 (CD80), as described in U.S. Patent Publication Nos. 2003/0124103 or 2002/0006413, the teachings of which are hereby incorporated by reference in their entirety.

In another embodiment of the compositions and methods described herein, the SV-BR cell is genetically modified to express a tumor antigen, such as a breast cancer antigen. In one embodiment, the tumor antigen is selected from the group consisting of HER2/neu, CA15.3, CD31, CD105, Tie-2/Tek, NY-ESO-1, MTA1 and MUC1. The cells of the present invention may be genetically modified to express one or more tumor antigens specific for a particular non-breast tumor. For example, if SV-BR-1 cells are used to treat a colon carcinoma, the cells can be genetically engineered to express tumor antigens expressed in a colorectal carcinoma. Exemplary tumor antigens suitable for an allogeneic tumor cell for treatment of a colorectal carcinoma include, for example, carcinoembryonic antigen (CEA), MUC1, Ep-CAM, HER2/neu, p53, and MAGE, including MAGE 1, 2, 3, 4, 6 and 12. Additional tumor antigens that are expressed in SV-BR cells can be identified using well known methods of screening for tumor antigens using, for example, tumor specific antibodies.

In another embodiment of the compositions and methods described herein, the SV-BR cell is genetically modified to express the Flt3 ligand, such as described in Braun et al. Hum Gene Ther. 1999; 10(13): 2141-51. In a related embodiment, the cells are genetically modified to express dominant negative forms of growth factors, such as dominant negative forms of EGF. In another embodiment, the cells express soluble forms of growth factor receptors or cytokine receptors which can titrate growth factors, such as soluble forms of her2, EGFR or VEGFR.

In another embodiment of the compositions and methods described herein, the SV-BR cell is genetically modified to express a cytokine. In a preferred embodiment, the cytokine is GM-CSF. Example 4 shows the construction of SV-BR-1-GM, an SV-BR-1 cell line which stably expresses GM-CSF. SV-BR-1-GM is deposited as American Type Culture Collection Accession No. PTA-1713. The genetic modification of cells to express GM-CSF has been described in U.S. Pat. Nos. 5,637,483, 5,904,920, 6,350,445, 6,033,674 and 5,078,996. In another embodiment, the cells are modified to express fragments of GM-CSF or fusion proteins between GM-CSF and other sequences, such as GM-CSF and a transmembrane domain.

In another embodiment of the compositions and methods described herein, the SV-BR cell is genetically modified to express an antibody or an antibody fragment. The antibody may be a monoclonal antibody, a humanized antibody, a chimeric antibody, a single chain antibody, an antibody fragment, or combinations thereof. The antibodies may be secreted by the SV-BR cells, or they may be expressed at the cell surface as transmembrane protein. The antibodies may be reactive, for example, towards cancer antigens, cytokines, growth factors or their receptors, or proteins expressed on the surface of T-cells.

In a another embodiment of the compositions and methods described herein, the compositions comprise SV-BR cells in which at least one polypeptide or an organic molecule is coupled to the surface of the tumor cell. For example, the polypeptide can be obtained using standard recombinant DNA technology and expression systems or it can be isolated from cells which express the polypeptide using standard protein purification techniques. For example, a B7 protein can be isolated from activated B cells by immunoprecipitation with an anti-B7 antibody. The isolated polypeptide can then be coupled to the SV-BR cell. The terms "coupled" or "coupling" refer to a chemical, enzymatic or other means (e.g. antibody) by which a polypeptide is linked to a tumor cell such that the polypeptide is present on the surface of the tumor cell. For example, the polypeptide can be chemically crosslinked to the tumor cell surface using commercially available crosslinking reagents (Pierce, Rockford Ill.). Another approach to coupling a polypeptide to a tumor cell is to use a bispecific antibody which binds both the polypeptide and a cell-surface molecule on the tumor cell. Fragments, mutants or variants of polypeptides which retain the ability to trigger a costimulatory signal in T cells when coupled to the surface of a tumor cell can also be used.

In yet another embodiment, the composition comprises SV-BR cells and an antineoplastic agent. Antineoplastic agents include, but are not limited to, chemical compounds, drugs, an antibodies or derivative thereof and RNAi reagents. Antineoplastic agents include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alpha, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

In one embodiment, the antineoplastic agent is 5-Fluorouracil, 6-mercatopurine, Actinomycin, Adriamycin®, Adrucil®, Aminoglutethimide, Anastrozole, Aredia®, Arimidex®, Aromasin®, Bonefos®, Bleomycin, carboplatin, Cactinomycin, Capecitabine, Cisplatin, Clodronate, Cyclophosphamide, Cytadren®, Cytoxan®, Dactinomycin, Docetaxel, Doxyl®, Doxorubicin, Epirubicin, Etoposide, Exemestane, Femara®, Fluorouracil, Fluoxymesterone, Halotestin®, Herceptin®, Letrozole, Leucovorin calcium, Megace®, Megestrol acetate, Methotrexate, Mitomycin, Mitoxantrone, Mutamycin®, Navelbine®, Nolvadex®, Novantrone®, Oncovin®, Ostac®, Paclitaxel, Pamidronate, Pharmorubicin®, Platinol®, prednisone, Procytox®, Tamofen®, Tamone®, Tamoplex®, Tamoxifen, Taxol®, Taxotere®, Trastuzumab, Thiotepa, Velbe®, Vepesid®, Vinblastine, Vincristine, Vinorelbine, Xeloda®, or a combination thereof.

In another embodiment, the antineoplastic agent comprises a monoclonal antibody, a humanized antibody, a chimeric antibody, a single chain antibody, or a fragment of an antibody. Exemplary antibodies include, but are not limited to, RITUXAN™ (rituximab), IDEC-C2B8, anti-CD20 Mab, PANOREX™ (edrecolomab), 3622W94, anti-EGP40 (17-1A) pancarcinoma antigen on adenocarcinomas, Herceptin, Erbitux, anti-Her2, Anti-EGFr, BEC2, anti-idiotypic-$GD_3$ epitope, Ovarex, B43.13, anti-idiotypic CA 125, 4B5, Anti-VEGF, RhuMAb, MDX-210 anti-HER2, MDX-22, MDX-220, MDX-447, MDX-260, anti-GD-2, QUADRAMET™ (samarium SM 153 Lexidronam), CYT-424. IDEC-Y2B8, Oncolym™, Lym-1, SMART™ M195 (humanized anti-CD33 antibody), ATRAGEN™ (all-trans retinoic acid— ATRA), LDP-03, anti-CAMPATH, ior t6, anti CD6. MDX-11, OV103, Zenapax, Anti-Tac, anti-IL-2 receptor, MELIMMUNE™-2, MELIMMUNE™-1, CEACIDE™ (antibody to carcinoembryonic antigen), PRETARGET™ (anti-CD20 fusion protein), NovoMAb-G2, TNT, anti-histone, Gliomab-H, GNI-250. EMD-72000, LYMPHOCIDE™ (Epratuzumab), CMA 676, Monopharm-C, anti-FLK-2. SMART™ ID10, SMART™ ABL 364, ImmuRAIT-CEA, or combinations thereof.

In yet another embodiment, the antineoplastic agent comprises an additional type of tumor cell. In a specific embodiment, the additional type of tumor cell is a MCF-10A, MCF-10F, MCF-10-2A, MCF-12A, MCF-12F, ZR-75-1, ZR-75-30, UACC-812, UACC-893, HCC38, HCC70, HCC202, HCC1007 BL, HCC1008, HCC1143, HCC1187, HCC1187 BL, HCC1395, HCC1569, HCC1599, HCC1599 BL, HCC1806, HCC1937, HCC1937 BL, HCC1954, HCC1954 BL, HCC2157, Hs 274.T, Hs 281.T, Hs 343.T, Hs 362.T, Hs 574.T, Hs 579.Mg, Hs 605.T, Hs 742.T, Hs 748.T, Hs 875.T, MB 157, SW527, 184A1, 184B5, MDA-MB-330, MDA-MB-415, MDA-MB-435S, MDA-MB-436, MDA-MB-453, MDA-MB-468 RT4, BT-474, CAMA-1, MCF7 [MCF-7], MDA-MB-134-VI, MDA-MB-157, MDA-MB-175-VII HTB-27 MDA-MB-361, SK-BR-3 or ME-180 cell, all of which are available from ATTC.

In another embodiment, the antineoplastic agent comprises a tumor antigen. In one specific embodiment, the tumor antigen is her2/neu. Tumor antigens are well-known in the art and are described in U.S. Pat. Nos. 4,383,985 and 5,665,874, in U.S. Patent Publication No. 2003/0027776, and International PCT Publications Nos. WO00/55173, WO00/55174, WO00/55320, WO00/55350 and WO00/55351.

In another embodiment, the antineoplastic agent comprises an antisense reagent, such as an siRNA or a hairpin RNA molecule, which reduces the expression or function of a gene that is expressed in a cancer cell. Exemplary antisense reagents which may be used include those directed to mucin, Ha-ras, VEGFR1 or BRCA1. Such reagents are described in U.S. Pat. No. 6,716,627 (mucin), U.S. Pat. No. 6,723,706 (Ha-ras), U.S. Pat. No. 6,710,174 (VEGFR1) and in U.S. Patent Publication No. 2004/0014051 (BRCA1).

In another embodiment, the antineoplastic agent comprises cells autologous to the subject, such as cells of the immune system such as macrophages, T cells or dendrites. In some embodiments, the cells have been treated with an antigen, such as a peptide or a cancer antigen, or have been incubated with tumor cells from the patient. In one embodiment, autologous peripheral blood lymphocytes may be mixed with SV- BR-1 cells and administered to the subject. Such lymphocytes may be isolated by leukaphoresis. Suitable autologous cells which may be used, methods for their isolation, methods of modifying said cells to improve their effectiveness and formulations comprising said cells are described in U.S. Pat. Nos. 6,277,368, 6,451,316, 5,843,435, 5,928,639, 6,368,593 and 6,207,147, and in International PCT Publications Nos. WO04/021995 and WO00/57705.

In another embodiment, the compositions comprising SV-BR cells further comprises one or immunostimulatory agents. As used herein, the term "immunostimulatory agent" is used in its broadest sense to mean a molecule that can positively effect the immunoresponsiveness of a subject.

An immunostimulatory agent can be an adjuvant. Adjuvants can include, for example, oil-in-water emulsions, water-in oil emulsions, alum (aluminum salts), liposomes and microparticles, such as, polystyrene, starch, polyphosphazene and polylactide/polyglycosides, squalene mixtures (SAF-I), muramyl peptide, saponin derivatives, cyclophosphamide, mycobacterium cell wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875, Freund's Adjuvant (IFA), bacille Calmett-Gerin (BCG), DETOX (containing cell wall skeleton of *Mycobacterium phlei* (CWS) and monophosphoryl lipid A from *Salmonella* Minnesota (MPL)), and the like (see, for example, Hoover et al., J. Clin. Oncol., 11:390 (1993); Woodlock et al., J. Immunotherapy 22:251-259 (1999)). Additional adjuvants are well known in the art (see, for example, Warren and Chedid, CRC Critical Reviews in Immunology 8:83 (1988); Allison and Byars, in Vaccines: New Approaches to Immunological Problems, Ellis, ed., Butterworth-Heinemann, Boston (1992)).

An immunostimulatory agent can also be a gene product that can be administered locally or systemically to a subject or expressed in a cell. A tumor cell or a normal cell such as a fibroblast or an antigen presenting cell can be genetically modified to express an immunostimulatory agent that is a gene product. Immunostimulatory agents that are gene products are known in the art and include, for example, the costimulatory B7 molecule (Baskar et al., Proc. Natl. Acad. Sci., USA 90:5687-5690 (1993); Townsend and Allison, Science 259:368-370 (1993); Tan et al., J. Immunol. 149:32217-3224 (1992), each which is incorporated herein by reference), autologous MHC class I and class II molecules (Plautz et al., Proc. Natl. Acad. Sci., USA 90:4645-4649 (1993); Hui et al., Fems Microbiol. Immunol. 2:215-221 (1990); Ostrand-Rosenberg et al., J. Immunol. 144:4068-4071 (1990), each of which is incorporated herein by reference), allogeneic histocompatability antigens such as HLA-B7 (Nabel et al., Proc. Natl. Acad. Sci., USA 90:11307-11311 (1993), which is incorporated herein by reference) and known tumor antigens (Finn, supra, 1993). A known tumor antigen can be particularly useful as an immunostimulatory agent.

A cytokine can be useful as an immunostimulatory agent. As used herein, the term "cytokine" refers to a member of the class of proteins that are produced by cells of the immune system and positively regulate or modulate effector functions of the immune response. Such regulation can occur within the humoral or the cell mediated immune response and can modulate the effector functions of T cells, B cells, macrophages, antigen presenting cells or other immune system cells. Specific examples of cytokines include, for example, interleukin-1, interleukin-2, interleukin-3, interleukin-4, interleukin-5, interleukin-6, interleukin-7, interleukin-10, interleukin-12, interleukin-15, gamma-interferon, tumor necrosis factor, granulocyte colony stimulating factor and granulocyte-macrophage colony stimulating factor. The use of GM-CSF as an immunostimulatory agent is described in U.S. Pat. No. 5,679,356. Furthermore, the cytokine can be administered in the form of an allogenic or a nonallogenic cell, including a fibroblast or a tumor cell, genetically modified to secrete the cytokine, such as described in U.S. Patent Publication No. 2002/0006413.

The invention also provides compositions comprising SV-BR cells and a physiologically acceptable carrier, such as compositions for inducing an immune response in a subject in need thereof. In some embodiments, the SV-BR cells of such compositions are SV-BR-1 or SV-BR-1-GM cells. A physiologically acceptable carrier includes any solvents, dispersion media, or coatings that are physiologically compatible, including any of the well known components useful for immunization. Additional physiologically acceptable carriers and their formulations are well-known and generally described in, for example, *Remington's Pharmaceutical Science* ($18^{th}$ Ed., ed. Gennaro, Mack Publishing Co., Easton, Pa., 1990) and *Handbook of Pharmaceutical Excipients* ($4^{th}$ ed., Ed. Rowe et al. Pharmaceutical Press, Washington, D.C.). The formulations can contain buffers to maintain a preferred pH range, salts or other components that present the cell to an individual in a composition that stimulates an immune response to the cells.

Administration of the therapeutic compositions of the present invention can be carried out using known protocols, at dosages and for periods of time effective to achieve the desired result. For example, a therapeutically effective dose of cells may vary according to such factors as age, sex and weight of the individual, the type of tumor cell and degree of tumor burden, and the immunological competency of the subject. Dosage regimens may be adjusted to provide optimum therapeutic responses. For instance, a single dose of SV-BR cells may be administered or alternatively several doses may be administered over time. Administration may be by injection, including intravenous, intramuscular, intraperitoneal, intracutaneous, intraarterial, peritoneal, intralymphatic and subcutaneous injections.

In a preferred embodiments, the compositions comprising SV-BR cells described herein are for inducing an immune response in a subject in need thereof wherein the subject is afflicted with a tumor or with cancer. In some embodiments, the tumor or cancer comprises cells which overexpress her2/neu. In preferred embodiments, the cancer is breast cancer, ovarian cancer or lung cancer. The breast cancer may comprise a ductal hyperplasia, a carcinoma in situ, an invasive ductal carcinoma, or a combination thereof.

In addition to breast cancer, ovarian cancer and lung cancer, the compositions provided by the invention for inducing an immune response in a subject in need thereof can be used to treat a subject afflicted with other types of cancers, and in particular, afflicted with an adenocarcinoma i.e. a malignant neoplasm of epithelial cells in glandular or gland-like pattern. Because many adenocarcinomas share antigens, the invention compositions that may be used as cancer vaccines can also be used to treat other types of adenocarcinomas if the tumors share antigens with the SV-BR-1 tumor cells. As used herein, a "patient having an adenocarcinoma" refers to an individual having signs or symptoms associated with an adenocarcinoma. Exemplary adenocarcinomas include those of colon, breast, lung, prostate, pancreas, kidney, endometrium, cervix, ovary, thyroid, or other glandular tissues.

Another aspect of the invention provides a nonhuman mammal comprising SV-BR cells. In a preferred embodiment, the nonhuman mammal is a rodent, such as a mouse. A mouse in which SV-BR cells have been introduced, such as by subcutaneous or intraperitoneal injection, may provide a convenient system in which to propagate the tumor cells. The nonhuman mammal may also comprise SV-BR cells which have been genetically modified, such as those modified to express nucleic acids or polypeptides e.g. SV-BR-1-GM cells. Furthermore, the SV-BR cells introduced into the mammal may be further selected to express, or cease to express, a particular phenotype, such as drug resistance, expression of a cancer antigen or ability to metastasize. Nonhuman mammals comprising SV-BR cells, or derivatives thereof, may also be used as model systems for tumorigenesis and for the identification of therapeutics for the diagnosis or treatment of cancer.

IV. Therapeutic Methods of Using Compositions of SV-BR Cells

The invention provides methods of using SV-BR cells, and in particular of using SV-BR-1 and SV-BR-1-GM cells, in therapeutic applications. The novel cells of the present invention can be used to increase tumor immunogenicity when used as cancer vaccines, and therefore can be used therapeutically for inducing or enhancing T lymphocyte-mediated anti-tumor immunity in a subject with a tumor or at risk of developing a tumor. A method for treating a subject with a tumor involves administering a therapeutically effective dose of a composition comprising SV-BR cells to the subject in need of such treatment.

One aspect of the invention provides a method of inducing an immune response in a subject in need thereof, comprising administering to the subject a therapeutically effective amount of a composition comprising at least one SV-BR cell, such as an SV-BR-1 cell or an SV-BR-1-GM cell. In a preferred embodiment, the subject is afflicted with a tumor and/ or with cancer. Any of the compositions described herein may be used in any of methods described herein.

A related aspect of the invention provides a method of treating a tumor in a subject in need thereof, comprising administering to the subject a therapeutically effective amount of a composition comprising at least one SV-BR, such as an SV-BR-1-GM or an SV-BR-1 cell. The SV-BR cells of the current invention may also be used for preventing or treating metastasis a tumor or for preventing or treating the recurrence of a tumor. They may also be used to ameliorate the symptoms of being afflicted with cancer. As described in the preceding section, nucleic acids may also be introduced into the SV-BR cells to allow the expression of a polypeptide, such as chemokine, a cytokine, a growth factor, a tumor antigen, a T cell costimulatory molecule or an antibody.

Prior to administration to the subject, the SV-BR cells may be treated to render them incapable of further proliferation in the subject, thereby preventing any possible outgrowth of the SV-BR cells. Possible treatments include irradiation or mitomycin C treatment, which abrogate the proliferative capacity of the tumor cells while maintaining the ability of the tumor cells to trigger antigen-specific and costimulatory signals in T cells and thus to stimulate an immune response. In a nonlimiting exemplary embodiment, cells are treated with X-ray doses of 100-200 Gray. In another embodiment, the SV-BR cells are treated with a crosslinking agent. U.S. Pat. Nos. 5,82,831 and 4,931,275 disclose methods of crosslinking cells. The cells may also be treated with a hapten to prevent their growth and improve immunogenicity as described in U.S. Pat. Nos. 6,403,104 and 6,248,585 and in U.S. Patent Publication 2003/0170756.

The SV-BR cells can be administered to the subject by injection into the subject. The route of injection can be, for example, intravenous, intramuscular, intraperitoneal, intracoronary, intramuscular, intraperitoneal, intracutaneous, intraarterial, peritoneal, intralymphatic or via a stent. Administration of the SV-BR cells at the site of an original tumor may be beneficial for inducing local immune responses against the original tumor. Administration of the SV-BR cells in a disseminated manner, e.g. by intravenous injection, may provide systemic anti-tumor immunity and, furthermore, may protect against metastatic spread of tumor cells from the original site.

The composition comprising the SV-BR cells may be administered at a dose sufficient to stimulate an immune response to one or more antigens of the SV-BR cell that are common to a tumor in the subject. One skilled in the art can readily determine an appropriate dose range for administering sufficient SV-BR cells to elicit an immune response. Such a dose can be at least about $1\times10^2$ cells, about $1\times10^3$, about $1\times10^4$ cells, about $1\times10^5$ cells, about $1\times10^6$ cells, about $1\times10^7$ cells, about $1\times10^8$ cells, about $1\times10^9$ cells, about $1\times10^{10}$ cells, or more. For example, as disclosed herein in the exemplification section, tumor cells may be administered at a total dose of about $10\text{-}20\times10^6$ cells per administration. In embodiments where additional non SV-BR cells are administered to the subject, such as autologous lymphocytes or other tumor cells, such cells may be formulated at individual doses such that an appropriate total dose of cells is administered to the subject. The compositions may be administered once to be subject, or more preferably at least twice. The compositions may be administered several times over a period, such as every week, two, three or four weeks or longer. Example 6 provides an exemplary treatment regimen. Another nonlimiting exemplary treatment plan is described by Emens et al., (2004) Human Gene Therapy 15:313-337.

It is understood by one skilled in the art that although the examples provided comprise the therapeutic use of unmodified SV-BR-1 cells, or of SV-BR-1 cells genetically modified to express GM-CSF, that such experimental designs may also be followed using any SV-BR, such as SV-BR cells which are modified to express other polypeptides. Further, other adjuvants or co-therapies such as those described herein may also be incorporated into such treatment plans.

In a specific embodiment, the subject receiving treatment according to the methods described herein is afflicted with, is suspected of being afflicted with, is likely to be afflicted with, or has been afflicted with at least one solid tumor or one non solid tumor, including carcinomas, adenocarcinomas and sarcomas. Nonlimiting examples of tumors includes fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, uterine cancer, breast cancer including ductal carcinoma and lobular carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, leukemias, lymphomas, and multiple myelomas. In a related embodiment, the tumor overexpresses cancer antigens which are expressed in SV-BR cells, such as her2/neu. In some embodiments, a subject is treated with an SV-BR that corresponds to the type of tumor for which treatment is needed. For example, an SV-BR ovarian cancer cell may be used to treat a subject afflicted with ovarian cancer, while an SV-BR breast cancer cell may be used In a preferred embodiment, the subject receiving treatment according to the methods described herein is afflicted with, is suspected of being afflicted with, is likely to be afflicted with, or has been afflicted with breast cancer. The breast cancer may be stage 0, I, II, III or IV breast cancer.

Subjects with Stage 0 breast cancer suffer from carcinoma in situ. Lobular carcinoma in situ (LCIS) refers to abnormal cells in the lining of a lobule, while carcinoma in situ (DCIS) is a precancerous condition in the lining of a duct. DCIS is also called intraductal carcinoma. These abnormal cells have not spread outside the duct to invade the surrounding breast tissue. However, if not treated, DCIS sometimes becomes invasive cancer. In stage I breast cancer, the tumor is no more than 2 centimeters and cancer cells have not spread beyond the breast. Stage II breast cancer is characterized by at least one of the following (a) the tumor in the breast is no more than 2 centimeters across and has spread to the lymph nodes under the arm; or (b) the tumor is between 2 and 5 centimeters (three-quarters of an inch to 2 inches) and may have spread to the lymph nodes under the arm; or (c) the tumor is larger than centimeters (2 inches) but has not spread to the lymph nodes under the arm.

Stage III may include a large tumor that has not spread beyond the breast and nearby lymph nodes. Stage IIIA means the tumor in the breast is smaller than 5 centimeters, the cancer has spread to the underarm lymph nodes, and the lymph nodes are attached to each other or to other structures. Or the tumor is large (more than 5 centimeters across), and the cancer has spread to the underarm lymph nodes. Stage IIIB means the tumor may have grown into the chest wall or the skin of the breast; or the cancer has spread to lymph nodes under the breastbone. Inflammatory breast cancer is a type of Stage IIIB breast cancer, were the breast appear red and swollen (or inflamed) because cancer cells block the lymph vessels in the skin of the breast. Stage IIIC refers to breast cancer that has spread to the lymph nodes under the breastbone and under the arm, or to the lymph nodes under or above the collarbone. The primary breast tumor may be of any size. Finally, stage IV is distant metastatic cancer where the cancer has spread to other parts of the body.

One embodiment of the methods described herein comprises administering to the subject at least one additional antineoplastic agent. Such agent may be administered at the same time, such as simultaneously, or essentially at the same time, such as in succession, as the composition comprising the SV-BR cells. If they are to be administered at the same time, the antineoplastic agent may be combined with the composition comprising the SV-BR cells. Alternatively, the antineoplastic agent may be administered as a separate composition.

The treatment regimen with the additional neoplastic agents may comprise different dosages and time intervals between administrations as that for the SV-BR cells. For example, a treatment regimen for the SV-BR-1-GM cells may comprise an administration of 10-20×10⁶ cells every two weeks, while administration of tamoxifen might comprise a daily dose of 20 mg. The additional neoplastic agents may be administered according to the dosing regimens suggested by their manufacturers or found to be effective in clinical trials.

In one embodiment, the antineoplastic agent is 5-Fluorouracil, 6-mercatopurine, Actinomycin, Adriamycin®, Adrucil®, Aminoglutethimide, Anastrozole, Aredia®, Arimidex®D, Aromasin®, Bonefos®, Bleomycin, carboplatin, Cactinomycin, Capecitabine, Cisplatin, Clodronate, Cyclophosphamide, Cytadren®, Cytoxan®, Dactinomycin, Docetaxel, Doxil®, Doxorubicin, Epirubicin, Etoposide, Exemestane, Femara®, Fluorouracil, Fluoxymesterone, Halotestin®, Herceptin®, Letrozole, Leucovorin calcium, Megace®, Megestrol acetate, Methotrexate, Mitomycin, Mitoxantrone, Mutamycin®, Navelbine®, Nolvadex®, Novantrone®, Oncovin®, Ostac®, Paclitaxel, Pamidronate, Pharmorubicin®, Platinol®, prednisone, Procytox®, Tamofen®, Tamone®, Tamoplex®, Tamoxifen, Taxol®, Taxotere®, Trastuzumab, Thiotepa, Velbe®, Vepesid®, Vinblastine, Vincristine, Vinorelbine, Xeloda®, or a combination thereof.

In another embodiment, the antineoplastic agent comprises a monoclonal antibody, a humanized antibody, a chimeric antibody, a single chain antibody, or a fragment of an antibody. Exemplary antibodies include, but are not limited to, RITUXAN™ (rituximab), IDEC-C2B8, anti-CD20 Mab, PANOREX™ (edrecolomab), 3622W94, anti-EGP40 (17-1A) pancarcinoma antigen on adenocarcinomas Herceptin, Erbitux, anti-Her2, Anti-EGFr, BEC2, anti-idiotypic-$GD_3$ epitope, Ovarex, B43.13, anti-idiotypic CA125, 4B5, Anti-VEGF, RhuMAb, MDX-210, anti-HER2, MDX-22, MDX-220, MDX-447, MDX-260, anti-GD-2, QUADRAMET™ (samarium SM 153 Lexidronam), CYT-424, IDEC-Y2B8, ONCOLYM™, Lym-1, SMART™ M195 (humanized anti-CD33 antibody), ATRAGEN™ (all-trans retinoic acid—ATRA), LDP-03, anti-CAMPATH, ior t6, anti CD6. MDX-11, OV103, Zenapax, Anti-Tac, anti-IL-2 receptor, MELIMMUNE™-2, MELIMMUNE™-1, CEACIDE™ (antibody to carcinoembryonic antigen), PRETARGET™ (anti-CD20 fusion protein), NovoMAb-G2, TNT, anti-histone, Gliomab-H, GNI-250. EMD-72000, LYMPHOCIDE™ (Epratuzumab), CMA 676, Monopharm-C, anti-ELK-2, SMART™ ID10, SMART™ ABL 364, ImmuRAIT-CEA, or combinations thereof.

In embodiments where the antineoplastic agent comprises a chemotherapeutic agent or an antibody, the antineoplastic agent may be formulated to increase potency or reduce side effects. In one embodiment, an antineoplastic antibody is formulated in a liposome for administration into the subject (Bendas G., BioDrugs. 2001; 15(4):215-24). In another embodiment, a chemotherapeutic drug is also formulated into a liposome (Gazibon et al., Adv Drug Deliv Rev. 2004; 56(8): 1177-92). U.S. Pat. No. 6,334,999 describes liposomal aerosols for delivery of chemotherapeutic retinoids to the lungs. Additional examples of liposomal formulations include pegylated-liposomal doxorubicin (Doxil®), liposomal doxorubicin (Myocet®), daunorubicin citrate liposome (DaunoXome®), pegylated liposomal doxorubicin (Caelyx), and liposome-encapsulated doxorubicin citrate (Myocet®). In other embodiments, the antineoplastic agent is pegylated, such as pegylated interferon alpha as described in U.S. Pat. No. 6,362,162. Accordingly, in one embodiment, the antineoplastic agent is pegylated, formulated in a liposome, or both.

In yet another embodiment, the antineoplastic agent comprises an additional type of tumor cell. In a specific embodiment, the additional type of tumor cell is a MCF-10A, MCF-10F, MCF-10-2A, MCF-12A, MCF-12F, ZR-75-1, ZR-75-30, UACC-812, UACC-893, HCC38, HCC70, HCC202, HCC1007 BL, HCC1008, HCC1143, HCC1187, HCC1187

BL, HCC1395, HCC1569, HCC1599, HCC1599 BL, HCC1806, HCC1937, HCC1937 BL, HCC1954, HCC1954 BL, HCC2157, Hs 274.T, Hs 281.T, Hs 343.T, Hs 362.T, Hs 574.T, Hs 579.Mg, Hs 605.T, Hs 742.T, Hs 748.T, Hs 875.T, MB 157, SW527, 184A1, 184B5, MDA-MB-330, MDA-MB-415, MDA-MB-435S, MDA-MB-436, MDA-MB-453, MDA-MB-468 RT4, BT-474, CAMA-1, MCF7 [MCF-7], MDA-MB-134-VI, MDA-MB-157, MDA-MB-175-VII HTB-27 MDA-MB-361, SK-BR-3 or ME-180 cell, all of which are available from ATTC.

In another embodiment, the antineoplastic agent comprises a tumor antigen. In one specific embodiment, the tumor antigen is her2/neu. Tumor antigens are well-known in the art and are described in U.S. Pat. Nos. 4,383,985 and 5,665,874, in U.S. Patent Publication No. 2003/0027776, and International PCT Publications Nos. WO00/55173, WO00/55174, WO00/55320, WO00/55350 and WO00/55351.

In another embodiment, the antineoplastic agent comprises an antisense reagent, such as an siRNA or a hairpin RNA molecule, which reduces the expression or function of a gene that is expressed in a cancer cell. Exemplary antisense reagents which may be used include those directed to mucin, Ha-ras, VEGFR1 or BRCA1. Such reagents are described in U.S. Pat. No. 6,716,627 (mucin), U.S. Pat. No. 6,723,706 (Ha-ras), U.S. Pat. No. 6,710,174 (VEGFR1) and in U.S. Patent Publication No. 2004/0014051 (BRCA1).

In another embodiment, the antineoplastic agent comprises cells autologous to the subject, such as cells of the immune system such as macrophages, T cells or dendrites. In some embodiments, the cells have been treated with an antigen, such as a peptide or a cancer antigen, or have been incubated with tumor cells from the patient. In one embodiment, autologous peripheral blood lymphocytes may be mixed with SV-BR cells and administered to the subject. Such lymphocytes may be isolated by leukaphoresis. Suitable autologous cells which may be used, methods for their isolation, methods of modifying said cells to improve their effectiveness and formulations comprising said cells are described in U.S. Pat. Nos. 6,277,368, 6,451,316, 5,843,435, 5,928,639, 6,368,593 and 6,207,147, and in International PCT Publications Nos. WO04/021995 and WO00/57705.

In one embodiments of the methods described herein directed to the treatment cancer, the subject is treated prior to, concurrently with, or subsequently to the treatment with the cells of the present invention, with a complementary therapy to the cancer, such as surgery, chemotherapy, radiation therapy, or hormonal therapy or a combination thereof.

In a specific embodiment where the cancer is breast cancer, the complementary treatment comprises breast-sparing surgery i.e. an operation to remove the cancer but not the breast, also called breast-sparing surgery, breast-conserving surgery, lumpectomy, segmental mastectomy, or partial mastectomy. In another embodiment, it comprises a mastectomy. A masectomy is an operation to remove the breast, or as much of the breast tissue as possible; and in some cases also the lymph nodes under the arm. In yet another embodiment, the surgery comprises sentinel lymph node biopsy, where only one or a few lymph nodes (the sentinel nodes) are removed instead of removing a much larger number of underarm lymph nodes. Surgery may also comprise modified radical mastectomy, where a surgeon removes the whole breast, most or all of the lymph nodes under the arm, and, often, the lining over the chest muscles. The smaller of the two chest muscles also may be taken out to make it easier to remove the lymph nodes.

In a specific embodiment, the complementary treatment comprises radiation therapy. Radiation therapy may comprise external radiation, where radiation comes from a machine, or from internal radiation (implant radiation, wherein the radiation originates from radioactive material placed in thin plastic tubes put directly in the breast.

In another specific embodiment, the complementary treatment comprises chemotherapy. Chemotherapeutic agents found to be of assistance in the suppression of tumors include but are not limited to alkylating agents (e.g., nitrogen mustards), antimetabolites (e.g., pyrimidine analogs), radioactive isotopes (e.g., phosphorous and iodine), miscellaneous agents (e.g., substituted ureas) and natural products (e.g., vinca alkyloids and antibiotics). In a specific embodiment, the chemotherapeutic agent is selected from the group consisting of allopurinol sodium, dolasetron mesylate, pamidronate disodium, etidronate, fluconazole, epoetin alfa, levamisole HCL, amifostine, granisetron HCL, leucovorin calcium, sargramostim, dronabinol, mesna, filgrastim, pilocarpine HCL, octreotide acetate, dexrazoxane, ondansetron HCL, ondansetron, busulfan, carboplatin, cisplatin, thiotepa, melphalan HCL, melphalan, cyclophosphamide, ifosfamide, chlorambucil, mechlorethamine HCL, carmustine, lomustine, polifeprosan 20 with carmustine implant, streptozocin, doxorubicin HCL, bleomycin sulfate, daunirubicin HCL, dactinomycin, daunorucbicin citrate, idarubicin HCL, plimycin, mitomycin, pentostatin, mitoxantrone, valrubicin, cytarabine, fludarabine phosphate, floxuridine, cladribine, methotrexate, mercaptipurine, thioguanine, capecitabine, methyltestosterone, nilutamide, testolactone, bicalutamide, flutamide, anastrozole, toremifene citrate, estramustine phosphate sodium, ethinyl estradiol, estradiol, esterified estrogens, conjugated estrogens, leuprolide acetate, goserelin acetate, medroxyprogesterone acetate, megestrol acetate, levamisole HCL, aldesleukin, irinotecan HCL, dacarbazine, asparaginase, etoposide phosphate, gemcitabine HCL, altretamine, topotecan HCL, hydroxyurea, interferon alfa-2b, mitotane, procarbazine HCL, vinorelbine tartrate, *E. coli* L-asparaginase, *Erwinia* L-asparaginase, vincristine sulfate, denileukin diftitox, aldesleukin, rituximab, interferon alfa-2a, paclitaxel, docetaxel, BCG live (intravesical), vinblastine sulfate, etoposide, tretinoin, teniposide, porfimer sodium, fluorouracil, betamethasone sodium phosphate and betamethasone acetate, letrozole, etoposide citrororum factor, folinic acid, calcium leucouorin, 5-fluorouricil, adriamycin, cytoxan, and diamino dichloro platinum, said chemotherapy agent in combination with thymosin$\alpha_1$ being administered in an amount effective to reduce said side effects of chemotherapy in said patient.

In another specific embodiment, the complementary treatment comprises hormonal therapy. Hormonal therapy may comprise the use of a drug, such as tamoxifen, that can block the natural hormones like estrogen or may comprise aromatase inhibitors which prevent the synthesis of estradiol. Alternative, hormonal therapy may comprise the removal of the subject's ovaries, especially if the subject is a woman who has not yet gone through menopause.

V. Additional Methods of Using Cell Lines

In addition to the methods of using the cells of the present invention for therapeutic treatments, the invention provides methods of using the cell lines in a variety of screening and/or diagnostic applications.

The cells of the present invention may be used to identify novel cancer antigens. Cancer antigens may be identified by comparing the mRNA or protein expression profile of SV-BR cells to that of a non-tumorigenic breast cells, or to nonmalignant transformed breast cells, such as by using DNA microarrays, 2-D gel electrophoresis, mass spectroscopy, western blots, or other immunological-based detection techniques known to one skilled in the art. Novel cancer antigens identified using the cells provided by the present invention may be used to develop therapies for the treatment of cancer, such as by generating antisense reagents or monoclonal antibodies specific for the antigen, or for diagnostic purposes.

The cells of the present invention may be used to screen for agents which modulate a cellular activity, such as cell growth, cell death, differentiation, cell division, metastasis, DNA repair, chemotaxis or extravasation. In one embodiment, an SV-BR cell is contacted with an agent and its cellular activity is compared to a cell that has not been contacted with said agent or is compared to another suitable control. In some embodiments, the screening for agents is performed on cells grown in cell culture, whereas other screening methods, such as those directed to the identification of agents which regulate metastasis or extravasation, may be performed in animals in which the SV-BR cells have been introduced, such as by subcutaneous injection into a mouse. The use of the cell of the present invention is not limited to any particular assay. By contrast, any assay known to one skilled in the art that uses a cell line may be adapted to use SV-BR cells.

The cells of the present invention may also be used for the identification of potential chemotherapeutic drugs: SV-BR cells are useful for screening chemicals suitable for the treatment of cancer and related diseases, by growing them in vitro in medium containing the chemical to be tested and then, after a suitable period of exposure, determining whether and to what extent cytotoxicity has occurred, e.g., by trypan blue exclusion assay or related assays (Paterson, Methods Enzymol., 58:141, 1979), or by growth assays such as colony forming efficiency (MacDonald, et al., Exp. Cell. Res., 50: 417, 1968), all of which are standard techniques well known in the art. Likewise, SV-BR cells may be used in studies of metabolism of carcinogens and other xenobiotics. For example, carcinogens and other xenobiotics may be added to the growth medium of cultures of these cells and then the appearance of metabolic products of these compounds may be monitored by techniques such as thin layer chromatography or high performance liquid chromatography and the like. The interactions of the compounds and/or their metabolites with DNA can then be examined.

The cells of the present invention may also be used to identify agents which regulate the expression or activity of genes. In one embodiment, an SV-BR cell is contacted with an agent, and the expression or activity of a gene is the SV-BR cell is compared to the expression or activity of that gene in an SV-BR cell that is not contacted with the agent, compared to a non SV-BR cell that has not been contacted with the agent, or compared to another suitable control. Expression of genes may be determined using any technique know in the art. Likewise, the activity of genes may be determined according to the particular activity of the gene. For example, enzymatic assays may be suitable when the gene is an enzyme and transcriptional assays or promoter occupancy assays may be suitable when the gene is a transcriptional regulator. In one specific embodiment, the gene for which modulatory agents are sought is her2/neu.

The cells of the present invention may also be used as a calibration standard in assays for gene expression, and in particular gene expression of cancer antigens, such as her2/neu. SV-BR-1 cells may be included in a kit which further comprises immunological reagents for the detection of cancer antigens.

Other technical terms used herein have their ordinary meaning in the art that they are used, as exemplified by a variety of technical dictionaries, such as the McGraw-Hill Dictionary of Chemical Terms and the Stedman's Medical Dictionary.

Exemplification

The invention now being generally described, it will be more readily understood by reference to the following examples, which are included merely for purposes of illustration of certain aspects and embodiments of the present invention, and are not intended to limit the invention, as one skilled in the art would recognize from the teachings herein above and the following examples, that other genetic modification, adjuvants, treatment regimens, assay systems, or data analysis methods, all without limitation, can be employed, without departing from the scope of the invention as claimed.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999; and PCR Protocols, ed. by Bartlett et al., Humana Press, 2003.

INCORPORATION BY REFERENCE

The contents of any patents, patent applications, patent publications, or scientific articles referenced anywhere in this application are herein incorporated by reference in their entirety.

EXAMPLE 1

Establishment and Characteristics of Parental Breast Carcinoma Cell Line (SV-BR-1)

Characteristics of Tumor

The parental cell line was established in 1999 from a 39 year old woman, married, a mother of 2, with no known history of or risk factors for sexually transmitted disease. The patient had previously-diagnosed breast cancer metastatic to brain, bone, lung, and skin. The specimen was isolated from a right chest wall lesion recurrent at the site of a previous right mastectomy. A rubbery pink-tan irregularly shaped tissue fragment preserved in formalin measuring 1×0.8×0.6 cm in greatest dimensions was sectioned and embedded. Microscopic sections revealed tissue fragments which were diffusely infiltrated by a malignant neoplasm. The tumor was characterized by numerous clusters and anastomosing trabecular cords of cells displaying enlarged vesicular, pleomorphic nuclei with one or more prominent nucleoli. The cells had moderate to scanty quantities of foamy cytoplasm. Focal necrosis was also present. The cell clusters were surrounded by dense fibrous connective tissues.

An unfixed portion of the tumor was further analyzed for response to several drugs. A specimen consisted of 1 piece of yellow, white, and red tissue, obtained from the right chest wall lesion. The piece was soft and sticky in texture, measured 0.8×1.4 cm, and weighed 0.47 gm. The specimen was minced to individual pieces smaller than one mm with surgical scissors and digested for 1.3 hours with collagenase-DNAse. Viable tumor cells were enriched by Ficoll-diatriozate centrifugation. Cytospin slides were prepared, air-dried, and stained with Fast Green/Hamatoxyline-eosin. On this cytology preparation obtained from mechanically-dissociated, enzyme-digested tissue, there was a collection of somewhat pleomorphic tumor cells, consistent with mammary carcinoma cells. Tumor cells were present as loose cell clusters (60% of total tumor cells) and, less commonly, as discohesive single cells (40% of total tumor cells). The tumor cells measured 22-25 microns in diameter and had N/N+C ratios of 0.6-0.8. Cytoplasm and chromatin each had a granular consistency. Nucleoli were variably prominent. There were no cells with large clear globular areas or secretory material within the cytoplasm. There was slight cytoplasmic and nuclear molding. Approximately 40% of the enriched tumor cell fraction consisted of normal-appearing connective tissue cells and inflammatory cells.

Cells were plated for testing in 3 different assay endpoints. In the DISC assay, the entire contents of the cell culture were cytocentrifuged onto permanent microscope slides and differentially stained to allow discrimination of normal and neoplastic cells and living and dead cells. The endpoint for cell death was delayed loss of membrane integrity, which has been found to be a surrogate for apoptosis. The MTT assay measures mitochondrial metabolism in the entire cell culture. The redox assay measures total metabolic activity in the entire cell culture, using the Alamar Blue reagent to index the oxygen reduction potential of the culture medium. Because of the very low yield of viable tumor cells, only a small drug panel could be tested. Additionally, some drugs could be tested only in a single assay system.

At the conclusion of the culture period, there was 10% spontaneous attrition in viable tumor cell numbers. Formazan signal in the MTT assay was moderate, reflective of moderate cell metabolism, and allowing for an MTT assay of good quality. Percentage of tumor cells as a percentage of total viable cells at the conclusion of the culture was approximately 85. DISC and MTT assays were in reasonably good agreement. The overall technical quality of the assays was good, marred only by the low yield of tumor cells, which severely limited the scope of testing.

Results were compared with a database of assays which had similar technical characteristics, as the technical characteristics of these assays influence the in vitro results, along with the intrinsic drug resistance of the tumor cells. By controlling for technical characteristics such as spontaneous cell loss, metabolic signal at the conclusion of the culture, and tumor cell clustering, biological correlations are improved. The results were as shown on the following table:

| DRUG OR COMBINATION | EXPECTED (Pre-Test) Response Rate | ASSAY RESULT | ASSAY PREDICTED RESPONSE PROBABILITY |
|---|---|---|---|
| Cyclophosphamide (4HC) | 25 | Sensitive | 55 |
| Carboplatin | 25 | Resistant | 5 |
| Doxorubicin | 30 | Intermediate | 30 |
| Etoposide | 25 | Sensitive | 55 |
| Fluorouracil | 20 | Intermediate | 20 |
| Gemcitabine + Cisplatin | 35 | Intermediate | 35 |
| Mitoxantrone | 30 | Intermediate | 30 |
| Taxol (Paclitaxel) | 30 | Sensitive | 62 |

-continued

| DRUG OR COMBINATION | EXPECTED (Pre-Test) Response Rate | ASSAY RESULT | ASSAY PREDICTED RESPONSE PROBABILITY |
|---|---|---|---|
| Vinorelbine (Navelbine) | 30 | Intermediate | 30 |

These results showed above-average activity for several drugs, including paclitaxel (Taxol), cyclophosphamide (4HC), and etoposide. In contrast, there was poor activity in the case of carboplatin. The remaining drugs had average or intermediate activity. The best drug in vitro was paclitaxel. DO WE NEED TO CITE WEISENTHAL Derivation of SV-BR-1 Cells To prepare the cell line, the remaining portion of the unfixed tumor specimen described above was processed by enzymatic digestion as follows. Sterile, fresh tumor was collected in transport medium of RPMI-1640 with 5% fetal bovine serum (Irvine Scientific) and transferred to sterile Petri dishes and exhaustively incised in a laminar flow hood under sterile conditions to produce small fragments. These fragments were treated with collagenase (0.15%) and DNAse (0.015-0.05%) (both from Sigma Chemicals) at 37° C. until the fragments disaggregated. Following enzyme dissociation, the material was filtered through Nytex mesh to remove the clumps and washed repeatedly with Hank's medium.

A portion of the tumor was frozen for future study and another portion used for vaccine preparation. Tumor cells were propagated in flat-bottom flasks (Corning) in RPMI-1640 (Irvine Scientific) or Dulbecco Modified Essential Medium with 10% heat-inactivated fetal calf serum (Irvine Scientific). MEM D-valine (Gibco) was used when necessary to selectively encourage tumor growth over fibroblast proliferation. No foreign suppliers of fetal calf serum were used. Medium supplements and their final concentrations were as follows—Gentamycin sulfate 80 mcg/ml (SoloPak. Cat 01402), L-glutamine 2 mM (Whittaker), sodium pyruvate 1 mM (Gibco, tissue culture grade), MEM non-essential amino acids 1% 0.1 mM (Gibco, tissue culture grade). Alterations in this procedure, either deletion of additives, change in concentrations, or other variation of techniques are not unexpected, given the empirical nature of tissue culture methodology and the dynamic ongoing changes in the technology. Cells were passaged after washing with warm sterile PBS (Bio Whitaker) and harvested after brief exposure to 0.05% Trypsin-EDTA (procine parvovirus tested, Irvine Scientific) to facilitate dislodgment. The batch yield was $150 \times 10^6$ at 100% viability. The cells were frozen in liquid nitrogen according to protocol.

The cells grew as an epithelial, adherent monolayer culture (Appendix G), have been passaged over 50 times with doubling time of 48 hours, and have been cloned for future studies. The cloned cell line, SV-BR-1, was further examined by microscopy. A cellblock was prepared from a sample of approximately 5 ml pink fluid with ivory-white, opaque pellet. The H & E section of the cellblock showed numerous single malignant cells. The tumor cells had one or more enlarged round to oval nuclei with finely granular to coarse chromatin, most of the nuclei of which contained a single macronucleolus. The tumor cells also demonstrated modest quantities of finely vacuolated cytoplasm. Immunohistochemical stains were performed on the paraffin embedded cellblock. Positive and negative controls were adequate. As an additional control, a section of the biopsy from which this cell culture was derived (BD99-1433) was mounted on each slide and stained simultaneously. A stain for low molecular weight keratin was moderately positive on both. A stain for estrogen receptors was negative on both. A stain for Her2/Neu was strongly positive on both.

The cell line grew readily in the nude mice and the resultant tumors had the histological appearance of human breast cancer, and were positive for human beta-actin by qualitative PCR, Medical Diagnostic Laboratories LLC. The Master Cell Bank (MCB) for SV-BR-1 cell line has been established and tested for sterility, mycoplasma, *T. pallidum*, endotoxin and human pathogens.

EXAMPLE 2

Tumor Formation of SV-BR-1 in Mice

Heterotransplantation studies with the human breast cancer cell line SV-BR-1 were performed. To demonstrate their malignant properties, $1 \times 10^7$ cultured SV-BR-1 cells were injected subcutaneously into 8 female 6-week old nude mice using a 0.2 mL inoculum. After 25 days, 7/8 mice showed tumors at the site of injection measuring 0.5 cm in diameter. At that time, tumors were removed from sacrificed mice and placed in buffered formalin overnight for histological examination. H & E slides of 5 micron tumor sections demonstrated vigorously growing tumors, consistent with the original diagnosis of human breast cancer. These studies provide a measure of the malignant origin of the cell line.

EXAMPLE 3

Treatment of Breast Cancer Patients with SV-BR-1 Cells

We have evaluated a cohort of breast cancer patients treated with a composition comprising SV-BR-1 cells, and administered in conjunction with GM-CSF. This particular cell line, designated SV-BR-1 is fast growing and has strong expression of the HER2/neu antigen, an immunogenic neoantigen that has been shown to be overexpressed by a high number of breast tumors (Szollosi J et al. Cancer Res. 1995; 55:5400-7). We have treated a small cohort of patients with very advanced stage IV breast cancer with a vaccine consisting of $10\text{-}20 \times 10^6$ viable, irradiated tumor cells (SV-BR-1) admixed with an equal number of cryopreserved peripheral blood lymphocytes obtained by leukapheresis. Patients were pretreated with low-dose cyclophosphamide 300 mg/m$^2$ 48-72 hrs prior to vaccine and received subcutaneous injections of GM-CSF just prior, and for 8 days after, vaccine inoculation. Toxicity included one patient with increasing ascites and abdominal discomfort during the GM-CSF injections and another patient who developed, following cyclophosphamide, exacerbation of pericardial effusion and atrial fibrillation, which spontaneously resolved. The median survival for 8 evaluable patients is 275 days (range 38-658 days), with 4 patients surviving more than 12 months. See FIG. 1 below.

EXAMPLE 4

Generation of (SV-BR-1-GM)

This example describes the generation of SV-BR-1 cells which express GM-CSF. Ready Made Competent Top 10 *E. Coli* bacteria were transformed with pcDNA 3.1/GS/GM-CSF Plasmid. The Genestorm hORF (human open reading frame) Expression Vector pcDNA 3.1/GS kit that includes competent Top 10 *E. coli* bacteria was purchased from Invitrogen (Catalog #H-M 13207M). The bacteria were transformed with supplied pcDNA 3.1/GS plasmid containing GM-CSF hORF and Zeocin resistance gene. The transformed bacteria were selected on Zeocin agar plates (Invitrogen; Q621-20), expanded in liquid Zeocin media (Invitrogen; Q620-20), mixed with equal amount of glycerol (Gibco, 15514-011)-SOB Media (Sigma H8032), aliquoted and stored in the −70° C. freezer.

The frozen transformed *E. coli* were expanded in Zeocin Liquid media. The extraction of the pcDNA3.1/GS plasmid was carried out using Invitrogen's S.N.A.P. Miniprep Kit (Cat #K1900-25) following the manufactures instructions. The extracted plasmid was aliquoted and stored in the −70° C. freezer. The quantity and purity of the extracted plasmid was determined by spectrophotometer. The plasmid sample was analyzed at 260 nm to determine the total yield of plasmid DNA and at 280 nm to assess the amount of contaminating proteins. The 260/280 ratio for the plasmid lot used for transfection was 1.7 (1.5 ratio is commonly accepted as a "cut-off" level of DNA purity).

The integrity of the extracted plasmid DNA was analyzed by gel electrophoresis. The samples were serially diluted 1:2 with sterile distilled water. For each lot of plasmid seven serial dilutions were prepared and ran along with 1 kb DNA ladder (Promega, Cat # G5711). The gel was stained with SYBR Gold Nuclei Acid Gel Stain and viewed using VisiBlue Transilluminator. The plasmid lot used for transfection of SV-BR-1 cell line appeared as a single band of approximately 3,000 bp and no lighter bands have been detected suggesting the integrity of a tested plasmid. The anticipated size of the plasmid according to manufacture (Invitrogen) is 4,000 bp. The difference can be explained by the circular shape of the plasmid compared to the linear DNA present in the ladder that may result in changed gel motility. The additional heavy bands can be explained by multiple plasmid DNA particles present in the sample.

Assessment of parental SV-BR-1 cell line sensitivity to Zeocin was performed. For selection of successfully transfected tumor cells the parental breast carcinoma (SV-BR-1) cells were cultured in the presence of various concentrations of Zeocin to determine the minimal concentration that kills most of the nontransfected cells. For transfection of SV-BR-1 with pcDNA 3.1/GS/GM-CSF plasmid, SV-BR-1 (passage 27) cells were harvested using 0.25% Trypsin-0.53 mM EDTA (Gibco, Cat # 25200, lot 1059547). The cells were seeded in a 12-well plate and incubated for forty-eight hours. Following incubation the cells were transfected with the pcDNA 3.1/GS/GM-CSF plasmid using LipofectAMINE 2000 reagent (Gibco, Cat #18292-011) according to the manufacture's directions. The cells were incubated with the transfection solution in the antibiotic free RPMI-10% FBS (Fetal Bovine Serum) (FBS, Irvine Scientific #3003, lot 300390135; RPMI, Irvine Scientific #9160, lot 916081255) for 24 hours.

For selection of permanently transfected SV-BR-1-GM clones and establishment of SV-BR-1-GM cell line, the permanently transfected tumor cells were selected by culturing in the RPMI-10% FCS containing 10 µg/ml Zeocin (selective media) for approximately one month. The surviving colonies were propagated in T-12, T-25, and T-75 flasks using selective mediator to establish a permanently transfected cell line (SV-BR-1-GM). After a few successful passages, the concentration of Zeocin in the media was decreased by roughly 50% to 4 µg/ml (maintenance media). The supernatant of cultured transfected tumor cells was tested for GM-CSF production by ELISA assay and found positive. The early passages of SV-BR-1-GM cell line were frozen in liquid nitrogen.

For preparation and validation of SV-BR-1-GM Master, Cell Bank (MCB)SV-BR-1-GM cell line (passage 4) was propagated in T-25, T-75, and T150 flasks using maintenance media (FBS, Irvine Scientific #3003, lot 300390135A; RPMI, Irvine Scientific #9160, lot 916010673). To confirm the production of GM-CSF, randomly selected flasks were incubated with the antibiotic-free RPMI-10% FBS for 72 hr. The supernatant was collected and the concentration of GM-CSF was determined by ELISA. The results showed that the GM-CSF is produced by cultured SV-BR-GM cells at the average concentration of 305.57 ng/ml (the assay sensitivity is 0.125-0.250 ng/ml). The propagated cells were harvested using 0.25% porcine Trypsin-1 mM EDTA (Gibco #25200, lot 1128850). The total yield was $115 \times 10^6$ cells at a viability of 97%. The cells were resuspended in the freezing medium (10% Dimethyl Sulfoxide, Sigma, #D2650, lot 111K2340 in the antibiotic-free RPMI-10% FBS) aliquoted into 77 cryovials at the concentration of $1.5 \times 10^6$ viable cells/vial.

The aliquots of a final vaccine product (before the freezing) were submitted for safety and sterility tests. General sterility testing according to 21CFR610.12 performed by the pathology department of St. Vincent Medical Center, mycoplasma testing was performed by culture at Specialty Laboratories, Santa Monica, Calif. No mycoplasma or other pathogens were identified by immunofluorescence testing done in our laboratory, nor by electron microscopy performed by Dr. Linda Kelly, Diagnostic Laboratory, USC.

Endotoxin testing performed in our laboratory. *Treponema pallidum* testing was performed on the cell line by qualitative PCR by Medical Diagnostic Laboratories LLC, Mt. Laurel, N.J. Also, one vial of MCB was taken for expansion in the antibiotic-free RPMI-10% FCS media for testing of HIV, HBV, HCV, and Human Parvo-virus performed by National Genetics Institute (Los Angeles, Calif.), HTLV, EBV, CMV, in vitro and in vivo adventitious agents performed by Apptec Laboratory Services (Camden, N.J.). The results of all tests were negative and the level of endotoxin in the MCB sample was 0.0176 ng/ml, which is much less than the commonly accepted "cut-off" level of 1 ng/ml.

EXAMPLE 5

Tumor Vaccine Lot Release Preparation and Validation

Each lot of tumor vaccine will be prepared by terminal expansion of a vial taken from the previously established, frozen Master Cell Bank (MCB) of SV-BR-1-GM cell line. For each lot preparation the cell line of transfected SV-BR-1 carcinoma cells will be propagated in T-75 and T150 flat-bottom flasks in antibiotic free RPMI-1640 complete culture medium until they reach the stage of 80-100% confluency. Prior to harvesting, the cells will be incubated with antibiotic free RPMI-1640 complete culture medium for 48 hr. The cells will be harvested using 0.05% Trypsin-0.53 mM EDTA solution (Gibco) and cell count and viability will be determined. The cells will be resuspended in freezing medium, aliquoted to $15 \times 10^6$ viable cells/ml, and frozen in liquid nitrogen. The aliquots of each lot will be submitted for general sterility testing, *Mycoplasma* testing and endotoxin testing. Only lots that pass those tests will be used. Tissue culture supernatant from each flask will be collected during harvesting, pooled, and the total volume of supernatant will be determined. The aliquot of supernatant will be taken to assess GM-CSF concentration, which will be determined by ELISA (sensitivity 0.125-0.250 ng/ml). The amount of GM-CSF in the 48 hour culture will be measured and normalized to the production of $1 \times 10^6$ tumor cells per 24 hr for each vaccine lot by the following formula: GM-CSF Concentration×Dilution Factor× Total Volume/(2×n), where n is a vaccine viable cell yield expressed in millions. While lot-to-lot variation of GM-CSF production is expected, we will reject any lot producing <40 ng or >500 ng GM-CSF/$10^6$ cells/24 hrs.

For vaccine formulation, two vials of SV-BR-1-GM cells will be removed from liquid nitrogen, thawed rapidly at 37° C., and washed with HBSS. Then, the cells will be resuspended in 20 ml of lactated Ringer's solution LRS). Tumor vaccine cells will be irradiated to 20,000 cGy in a GammaCell device, a device calibrated routinely. The total cell count and viability will be determined. Only lots with viability >70% will be considered useable for clinical application; those lots with less than this value will be discarded. After counting, the cells will be washed and resuspended in LRS—Intron A solution at a final concentration of 10,000 IU/ml Intron A and $20 \times 106$ viable irradiated tumor cells/ml. A total volume of 1.2 ml ($24 \times 106$ cells) will be prepared and the vaccine will be distributed into two 1 cc syringes, 0.5 ml each, and submitted for injection.

The remaining aliquot of 0.2 ml will be used for gram staining and endotoxin testing. All steps will be performed aseptically. The gram staining and endotoxin testing will be performed prior to final product release. Only vaccines that pass those tests will be injected. Vaccine will be prepared in sufficient quantity to retain a small aliquot of ~10% of the inoculum to be stored sterility over liquid nitrogen.

EXAMPLE 6

Treatment of Breast Cancer with SV-BR-1 Modified to Secrete GM-CSF

The efforts of many researchers have suggested the presence of breast cancer associated antigens, including CEA, MUC1, and others[16]. A comprehensive review is beyond the scope of this protocol; Renkvist et al have made a catalog[17], available online (http://www.institutotumori.mi.it) of tumor associated antigens recognized by T-cells, of which breast-cancer related antigens are frequently noted. A compilation of serologically defined antigens is also available online (www.licr.ort/SEREX.html).

Previously, the establishment of a large library of breast cancer cell lines, together with available autologous serum, supported the writer's earlier studies of tumor-specific host immune responses[18]. Indirect immunofluorescent antibody assays detected autologous reactivity to established breast cancer cell lines in 8 of 10 patients; reactivity remained present after absorption with heterophile antigens, normal breast tissue, and AB+human red cells. These reactions occurred in 40-66% of allogeneic sera samples from breast cancer patients, and were not explainable as reactions to CEA. Additional work indicated both humoral and cell-mediated reactivity[19, 20] to antigens related to mouse mammary tumor virus. There has been renewed interest[21] in the possibility that human breast cancer may involve an agent similar to mouse mammary tumor virus. Those early serological studies as well as in vitro studies of cell-mediated immunity were consistent with this still-unresolved hypothesis.

Breast cancer may have antigens related to the Thompson-Friedenreich blood group antigen[22]. The project investigator has had an interest in these antigens, and performed a small survey of cellular and humoral responses to a commercial "T-antigen" preparation (Wiseman et al, unpublished results). While this investigation was inconclusive, others have pursued this area, even to the point of very large Phase III clinical trials[23].

Given the existence of known and putative breast-cancer associated antigens, there are many options for creating cancer vaccines[6]. Questions persist regarding the use of whole-cell vs. tumor extracts, autologous antigens vs. chemically defined antigens, and other treatment variables. Issues of dose, route, schedule and duration of therapy require much further investigation, especially in the absence of a commonly-accepted surrogate marker of immune response[24, 25]. Even if available, the evaluation of response and survival is the ultimate, practical outcome measure.

Vaccine therapy has been associated with regression of bulky, macroscopic tumor. Our group recently described such results, notably, in a melanoma patient, involving a change in tumor volume on the order of 800 cc. Others have also reported tumor regressions in advanced cancer, and in particular, breast cancer. Jiang et al. reported using subcutaneous injections of autologous and allogeneic MCF-7 breast cancer cells, together with CA15-3, CEA, CA125 plus IL2 and GM-CSF in 42 patients with advanced breast cancer, and observed clinical regression in 2 patients, one of whom had complete disappearance of hepatic metastases[26]. Krause et al. have been applying a dendritic vaccine program to breast cancer as well as melanoma[27] and have observed several breast cancer patients with major regression of advanced, metastatic tumor, one of whom had a response of such intensity as to precipitate tumor lysis syndrome[28]. The early reports on sialyl-Tn vaccine identified partial responses in 3 of 12 patients[29] although, as mentioned, a Phase III clinical trial that followed failed to achieve the predetermined statistical endpoints of improvement in time to disease progression and overall survival (www.biomira.com).

Disis et al. have demonstrated that frequent and durable immune responses to HER2/neu can be generated[30]. This study also employed GM-CSF in conjunction with peptides of the HER2/neu receptor antigen. Of 64 patients with overexpression of HER2/neu (including ovarian and non-small cell lung cancer), 92% demonstrated immune responses to the immunizing antigen, and persistence of same for at least 12 months. Moreover, the phenomenon of epitope-spreading was documented as well. The overall implications for clinical outcome remain inconclusive, however.

Whole cell vaccines continue to hold appeal for vaccine studies, especially given the very recent report of 3 of 33 complete remissions in lung cancer with a whole-cell vaccine transfected with GM-CSF[31]. We note that the plasmid-transfection methodology used here has the potential to provide a more stable and more sustained level of GM-CSF production. Given our current lack of knowledge of the presence and distribution of the relevant tumor-associated antigen(s)[32], whole cells may have the advantage of providing a large repertoire of both membrane and cytoplasmic antigens, and, while some antigens have been characterized, it is likely many more remain to be identified.

This Phase Ib investigation is designed to provide safety and feasibility experience in treating stage IV breast cancer with a whole-cell vaccine, SV-BR-1-GM, a breast cancer cell line genetically engineered to secrete GM-CSF and consequently augment dendriteactivity[1, 2, 3, 4]. The initial stage of the study will accrue 9 evaluable patients, each of whom will receive 6 intradermal inoculations, at 2-week intervals×3, then monthly×3. To facilitate the immune response, patients will be pretreated with low-dose cyclophosphamide to help down-regulate suppressor-cell mechanisms[5, 6, 7, 8] 48-72 hours prior to each vaccine injection. Low-dose interferon-alpha (Intron-a, Schering) is used as an adjuvant[9, 10] admixed with each vaccine, and again given by intradermal injection to the inoculation site 48 hours later.

Development of Grade IV (or Grade III allergy/hypersensitivity) toxicity will truncate patient accrual; development of new or progressive tumor, or development of Grade III toxicity (or Grade II allergy/hypersensitivity) will truncate further inoculations to any particular patient. Provided all nine patients have tolerated the procedure safely and without significant toxicity, an additional cohort of 15 persons (to a total of 24) may be entered if there is any preliminary evidence of clinical response OR of anti-tumor immunological response as measured by delayed-type hypersensitivity (DTH) skin tests or in-vitro assays.

This experimental plan is designed according to the recommendations of Simon et al, [11, 12], a plan to maximize data-gathering, minimize risk, and evaluate an immunological therapy for which the classical phase I assessment of maximum tolerated dose is not applicable. The plan has the potential to provide a 95% confidence level of identifying a regimen with an activity of 25% or more.

We have reviewed the reports on cancer cell vaccines genetically modified to produce various cytokines, including GM-CSF[34]. These reports add to the understanding of safety and tolerability for GM-CSF-transfected whole-cell vaccines and reinforce the notion that the method of GM-CSF introduction appears to have several important advantages over subcutaneous injections of the cytokine: a) it is less labor-intensive, b) it is less likely to cause the side-effects associated with systemic GM-CSF injections, c) local cytokine concentration is more stable and long-lasting, and d) cytokine is directly released to activate APC at the site of vaccine injection.

Because of the current data regarding GM-CSF, and because we have developed in our laboratory a breast cancer cell line with several desirable features, we propose this clinical investigation. We will use this breast cancer cell line transfected ex vivo with the GM-CSF gene. The vaccine will be injected intradermally to potentiate activation of in-situ APC. Interferon-α will be added as an adjuvant, since it serves as a "danger signal" and has been shown to facilitate the maturation of APC precursors into functionally active dendrites[10]. Patients will be premedicated with low-dose cyclophosphamide because of its effect on suppressor activity[7-9, 35] and potential synergism with the vaccine process by fostering cytokine responses, induction of MHC antigens on tumor cells or other mechanisms not yet identified[36].

Study Design

Figure 2:
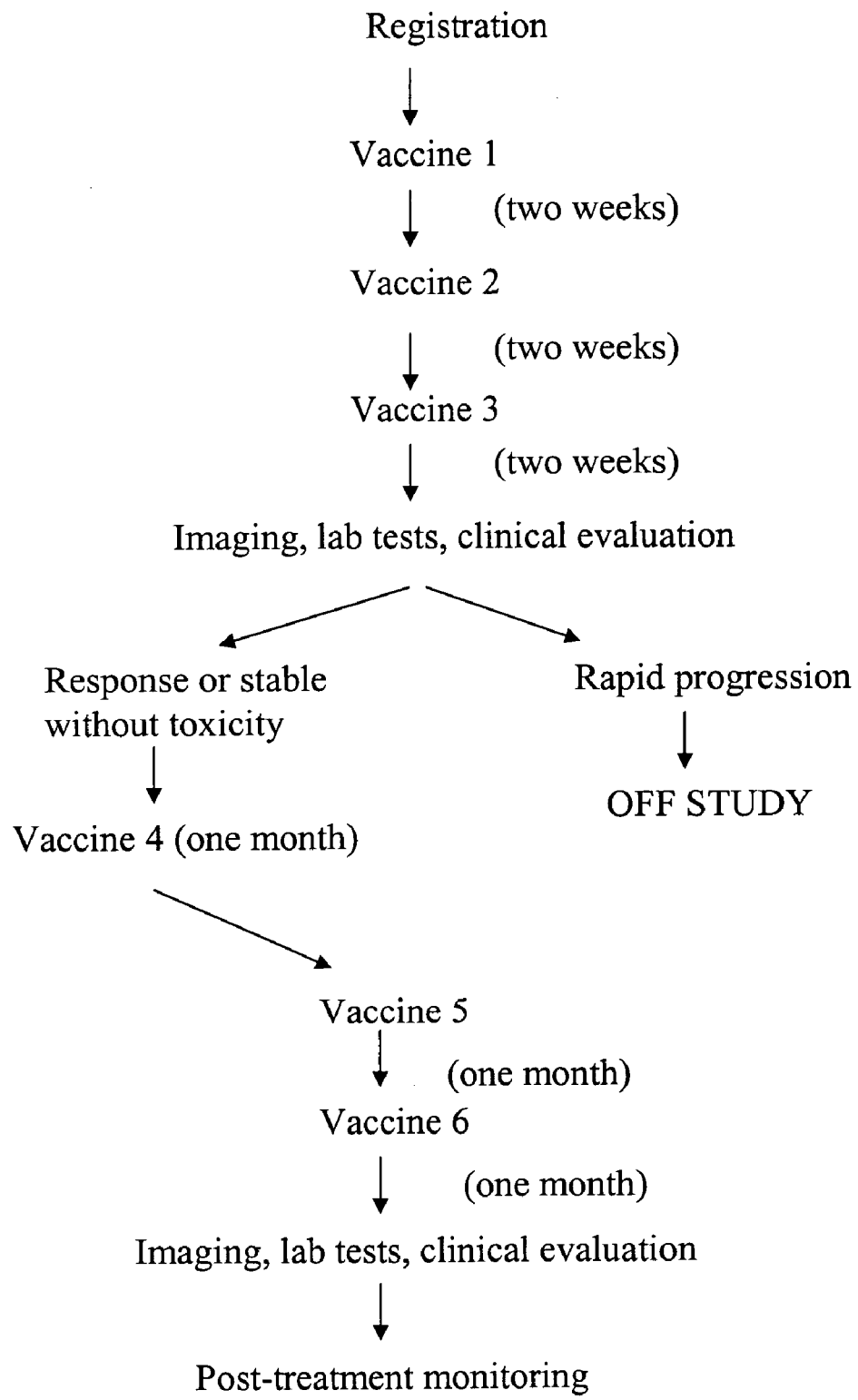
FIG. 2 depicts the program schema for breast cancer immunotherapy using SV-BR-1-GM cells.

The protocol is a one-arm, "optimal 2-stage trial" designed to assess safety but also to minimize the number of patients at risk if there is no evidence of activity[12]. Patients receive vaccine every 2 weeks for 3 inoculations during the first month, then monthly for 3 more treatments, provided no evidence of excess toxicity or of new or enlarging tumor, for a total of 6 vaccines over a 5-month period. The program Schema is diagramed in FIG. 2. NOTE: Grade III or IV toxicity at ANY step will warrant special review; see Toxicity Insofar as this is a preliminary safety/toxicity study, clinical response, duration of response, and survival are not primary endpoints of the protocol, but such data will be monitored, as is the practice of our clinic. Similarly, quality of life may be assessed both by clinician's evaluation and also by a standardized questionnaire (SF-36 Health Survey).

The protocol begins with characterization of the patients' clinical and immunological status. The study employs intradermal immunization with irradiated, GM-CSF-producing breast cancer whole-cell vaccine, admixed with interferon-alpha (Intron-A, Schering), pretreatment with low-dose cyclophosphamide, and boosting with a injection of low-dose interferon to the inoculation site after 48 hours.

Pre-vaccine low-dose cyclophosphamide is given by intravenous infusion 48-72 hours before vaccine. Low-dose cyclophosphamide may have multiple modes of action, including the down-regulation of immune suppressor-cell activity[7, 8] induction of type 1 interferon[9], upregulation of MHC antigens[37] reversal of tolerance via upregulation of tumor-specific CD4+ helper activity[38], and/or by other mechanisms not yet studied. Clinical evaluation and IFN-alpha booster injection in situ at the vaccination site occurs 48 hours later. Interferon is included because of its effect in augmenting dendrite maturation[10, 39, 40].

Three inoculations are administered initially, at 2-week intervals. At week eight, patients change schedule to receive inoculations at monthly intervals, for 3 months, provided there is no evidence of excess toxicity (see below, Toxicity/Off-study considerations) or new or enlarging sites of tumor.

Endpoints

The primary endpoint is to assess clinical toxicity and feasibility of administration of this regimen with accrual of at least 9 evaluable patients; and the secondary endpoints are to evaluate clinical responses, if any, after 3 vaccines and at the conclusion of study, i.e., after inoculation #6; and to assess immune responses, if any, as measured by DTH skin tests, ELISA assays for antibody to tumor vaccine, and flow-activated cell sorter assay for vaccine antigen-reactive T-cells.

Patients will be recruited by IRB-approved advertisement, submission of the protocol to the NCI PDQ, and lectures and seminars by the investigators that might lead to referrals, as well as from the private practice of this investigator. Because this study is designed to evaluate a disease with fewer than 5% occurrence in men, for the purpose of comparability, no males will be entered at this time. Persons of all racial and ethnic groups are eligible for treatment contingent on meeting all eligibility criteria. No convincing data exists to limit or to encourage accrual of any particular racial or ethnic group. To be eligible for consideration patients must: be age 18 or older; have histological confirmation of breast cancer on record; have Stage IV breast cancer manifested as local recurrence and/or distant metastases indicating failure of previous treatments for which curative or reliably effective palliative surgery, radiation therapy, or medical therapy is not available; have expected survival of at least 4 months; have adequate performance status (ECOG 0-2 or Karnofsky above 60); have previously received currently-accepted first-line chemotherapy, (e.g. anthracyclines, taxanes,) whether or not previous treated on adjuvant chemotherapy; have previously received currently-accepted hormonal therapy if appropriate; have provided written informed consent.

The following will not disqualify patients: cytology-documented malignant effusions, histology-proven marrow involvement, or other evaluable but not measurable metastatic disease; stable brain metastases previously treated, not requiring corticosteroids, and not showing radiological or clinical deterioration for 6 weeks—Recent treatment with gamma knife or IMRT, since the volume of irradiation is very small compared to classic teletherapy, may be entered on protocol as soon as feasible provided there has been recovery from known or anticipated toxicities; absence of HLA A2 allele; inhalation steroids for respiratory hypersensitivity (e.g. triamcinolone nasal or pulmonary inhalers); previous treatment with trastuzamab or other biological therapies, provided 3 or more weeks have passed since the last treatment and the patient has recovered from all known or anticipated toxicities; persons receiving pamidronate, bisphophonates, or other supportive measures are to continue such while on protocol; patients with "bone-only" metastatic breast cancer will be eligible provided the other criteria are satisfied.

The following exclusion criteria apply to this study: concurrent or recent chemotherapy (within 3 weeks), hormonal therapy, XRT, immunotherapy, or general anesthesia/major surgery. Patients must have recovered from all known or expected toxicities from previous treatment and passed a treatment-free "washout" period of 3 weeks before starting this program (8 weeks for persons receiving nitrosourea or mitomycin); history of anaphylactic reaction to any known or unknown antigen; history of clinical hypersensitivity to GMCSF, interferon, yeast, beef or to any components used in preparation of vaccine; BUN >30 and a creatinine >2; absolute granulocyte count <1000; platelets <100,000; bilirubin >2.0; alkaline phosphatase >5× upper limit of normal (ULN); ALT/AST >2×ULN; proteinuria >1+ on urinalysis or >1 gm/24; woman of childbearing potential unless she (a) agrees to take measures to avoid becoming pregnant during the study and (b) has a negative serum pregnancy test within 7 days prior to starting treatment; women who are pregnant or nursing; patients with concurrent second malignancy.

Persons with previous malignancies effectively treated and not requiring treatment for >24 months are eligible, provided there is unambiguous documentation that current local recurrence or metastatic site represents recurrence of the primary breast malignancy; Patients must not be HIV positive; patients must not require anticoagulation, systemic steroids, or be on treatment for rheumatological, psychiatric, or other clinically progressive major medical problems; patients must not require beta-blockers for control of mild hypertension or other indications, as these agents might compromise use of epinephrine for the rare possibility of anaphylaxis. (Hypertension controlled by other agents does not disqualify, provided other criteria are met.).

Treatment Plan

Subjects will undergo staging and baseline studies within 14 days of starting treatment. Cyclophosphamide (Cytoxan) will be administered at 300 mg./m$^2$ I.V., 1× only, 48-72 hours before each vaccine. Tumor vaccine Cycle I will be administered on Day 1 via intradermal injection immediately before inoculation, subjects will have delayed-type hypersensitivity skin tests to $1.0(+/-0.2)\times10^6$ non-transfected SV-BR-1 breast tumor cells and to recall antigens.

Patients will be receive $20(+/-2)\times10^6$ viable, irradiated transfected SV-BR-1 breast tumor cells in a total volume of 2.0 ml Ringer's lactate admixed with 10,000 u of interferon-alpha (Intron-A, Schering) as an adjuvant. Vaccine will be divided into four aliquots of 0.50 ml each and injected intradermally into the anterior skin of the right and left thigh and over the right and left scapula. Preparation of the vaccine comprising SV-BR-1 cells genetically modified to express GM-CSF is described in the previous examples. The preparation of transfected SV-BR-1 tumor cells is described in the preceding experimental examples.

Forty-eight to seventy-two hours later, the patient will receive 2,500 u of interferon-alpha in 0.10 ml into each vaccine site. Dose reduction of 50% will ensue if patient has excessive local toxicity, as further discussed below (see Toxicity). It is expected that treatment will be performed in outpatient facilities, and hospitalization is not expected unless complications develop. Treatment will be administered with appropriate medical supervision and the close availability of support measures.

Tumor Vaccine, Cycle II and following, will occur at 2-week intervals from initiation of treatment for a total of 3 cycles, then monthly, provided there has not been undue toxicity (defined under Treatment Plan, Toxicity) and provided re-staging studies do not demonstrate progressive disease according to RECIST criteria. Restaging will occur at week 6, before beginning monthly maintenance doses (at week 8) and 2 weeks after completing the expected total of 6 treatments (week 22). Refer to the study calendar for a complete schedule.

Evaluation

The evaluation of patients, preparation of tumor cell vaccine, and conduct of the tumor-vaccine specific immunological tests will be performed at the St. Vincent Medical Center implemented by applicants. Data collection will be accomplished with the assistance of pre-prepared clinical report forms in addition to standard medical records. Because immunological therapies may sometimes require a lengthy time interval to observe response, our concept emphasizes observation over a period of several months. The key evaluation is that which occurs two weeks after the last vaccine. The evaluation that occurs at week 6 before going to monthly maintenance is to identify if there is rapid tumor growth refractory to current treatment or requiring other prompt interventions.

Measurable lesions together with immunological indices will be evaluated after 6 weeks from initiation of therapy and two weeks after receiving an additional 3 treatments, given at monthly intervals (Week 18). Performance status and quality of life will be documented monthly using the Karnofsky Scale and the WHO performance scale, and the widely used, validated[41] SF-36 questionnaire.

Tumor-specific immunological response: The HER2/neu antigen is very highly expressed in the particular cell line we plan to study. While it is expected that other relevant antigens may be present as well, the presence of at least this one, well-characterized protein will provide the study with a defined candidate antigen. We will try to evaluate the generation of immune responses against the tumor cell-line, and, if such responses are present, identify if directed against HER2/neu or non-HER2/neu epitopes. Clinical immunotherapy studies using purified HER2/neu antigens have reported up-regulation of T-cell responses to antigens quite unrelated to those used for immunization, the phenomenon of "epitope spreading,"[42] and this phenomenon may or may not be identified in this trial. We will collect information regarding patients' HER2/neu status and treatment with trastuzamib for data analysis, but do not exclude or stratify otherwise qualified patients by these criteria.

Testing and Monitoring

The patient evaluations include the following:

(a) Complete physical exam, including Vital signs; Performance status; Repeat with pertinent physical exam q 2 week or concomitant with vaccine maintenance therapy.

(b) CBC, differential, platelets, T and B subsets, comprehensive metabolic biochemical profile, uric acid, cholesterol, LDH, SGPT, GGTP, urinalysis, q 4 wk. or as clinically indicated.

(c) Quality of Life Questionnaire SF-36.

(d) Karnofsky scale rating.

(e) Chest X-ray at baseline, at the 6-week evaluation, and after study conclusion, week 22.

(f) CT scan abdomen and pelvis at baseline, at the 6-week evaluation, and after study conclusion, week 22 Isotope bone scan, PET scan (or FDG SPECT scan) and/or selected bone X-rays as appropriate.

(g) CEA serology, at baseline, at the 6-week evaluation, and after study conclusion, week 22

(h) Brain scan MRI or CT technique if clinical indication of neurological symptoms (i) Serum beta-HCG pregnancy test within 7 days before starting treatment for women of childbearing potential (j) Immunohistological evaluation, if not already performed, of HER2/neu expression from whatever previous biopsy was diagnostic of breast cancer; when possible, FISH methodology is preferred.

(k) Patients will be evaluated by the physician at every 2 weeks (or more often) during the initial phase of therapy (l) Data will be recorded on clinical report forms, which are also designed to define to remind the clinician of relevant toxicity evaluations.

(m) Anergy skin testing will be performed at the first, third, and last vaccine inoculation. Punch biopsy of a vaccine injection site, to evaluate for histology and characterization of cell infiltrate will also be performed at those visits, 48-72 hrs after inoculation. If available, $1 \times 10^6$ autologous irradiated tumor cells, as well as non-transfected SV-BR1 will be injected at time of the last vaccine, as described below.

(n) Antigens preparations and suppliers as determined by availability and by St. Vincent Medical Center Formulary: PPD 5 u/0.10 ml (or 1 u/0.10 ml, for previous BCG treated patients or known strong reaction to PPD) (Parkdale, Pharmaceutical, Inc.), Trichophyton 1:500/0.02 ml (Alk-Abello Round Rock, Tex.), Mumps 0.1 ml (Connaught Labs, Swiftwater, Pa.), Candida 0.10 ml (Allermed Laboratories Inc. San Diego, Calif.).

(O) Delayed-type hypersensitivity (DTH) reaction: tumor-specific: An aliquot of $1 \times 10^6$ viable non-transfected irradiated SV-BR-1 tumor cells, and irradiated autologous tumor cells (if available, similarly prepared) each in 0.1 ml of LRS will be injected intradermally into the patient's arm on the day of vaccine injection.

(p) At the time of testing, the injection will be observed also for the possibility of acute hypersensitivity reactions, and the patient will be monitored for 20 minutes before proceeding with vaccine injection.

(q) Delayed type hypersensitivity will be assessed at 48 and 72 hours after injection.

(r) The diameter of induration AND erythema will be measured at these points; while most investigators consider induration as the relevant response a recent paper involving melanoma demonstrated improved survival was highly correlated to skin test responses as measured by erythema only[43]

(s) Acute hypersensitivity is defined as a 2× increase in area of induration of the inoculation within one hour, or the development of systemic symptoms of wheezing, additional zones of urticaria remote from the injection site, or generalized pruritus.

(t) Such findings will be followed by evaluation by a consultant allergist, reported to the FDA as an adverse event, and further treatment on this protocol will not be administered, unless specifically permitted after FDA review.

Tumor-Vaccine Specific Immunological Response:

(u) Serum antibodies to SV-BR-I whole cell antigens, and to HER2/neu. The antibody titers will be determined by ELISA.

(v) Peripheral blood antigen-reactive T cells to SV-BR-I cell: The antigen reactive T cells will be determined by flow cytometry ELISA.

(w) Preparation of autologous tumor for immunologic assays: Autologous tumor, if available, will be processed to provide single-cell suspension and stored according to the procedures used to establish the SV-BR1 line. Cells so obtained will be utilized in conjunction with other targets in antibody and cell-mediated immunity assays. Specimens so processed will be acceptable only if obtained for medically justified reasons (for example, drainage of effusions, toilet mastectomy for hygiene). Tumor harvesting is not required for entry into the protocol.

(x) Autologous lymphocytes will be collected at the time of baseline analysis and at intervals described (refer to Calendar). Blood is collected in heparinized tubes, lymphocytes separated by Ficoll-hypaque technique and stored over liquid nitrogen. Serum is collected in standard redtop tubes and stored at −70 degrees C. Clinical response definitions (as per RECIST criteria). The following is a capsule summary of these response criteria—Please see Therasse et al for full description[44].

Measurability

Measurable disease: require such features so as to be accurately measurable (+/−10%) in at least one dimension on CT (</=1.0 cm cuts), MRI, plain X-ray, or medical photographs AND have a major axis of 2.0 cm or more. Tumor lesions seen on images obtained by spiral CT (with a 5 mm contiguous reconstruction algorithm) must be 1.0 cm or greater. Ultrasound imaging will be permitted only for superficial lesions. Bone lesions will not be considered under these criteria.

Non-measurable disease: includes bone lesions, effusions, poorly-demarcated pulmonary infiltrates, and lesions <1.0 cm by radiological imaging.

Objective status at examination: Target lesions are to be defined as measurable lesions, up to 10 sites per patient and no more than 5 sites in any one organ. Measurements of target lesions must be provided at evaluations pre-treatment, at 6 weeks, and at the conclusion of the 12-week treatment schedule. Development of new lesions must be documented.

Responses

Responses are to be defined as follows: (for application to manuscripts or submission for presentation at scientific meetings, only CR/PR will be considered "responses").

Responses For Target Lesions include the following:

Complete response: Complete disappearance of all measurable and non-measurable disease AND absence of any new lesions. If serologic markers, e.g. CEA, or CA 27.29 were elevated prior to treatment, these values must have normalized.

Partial response: Greater than or equal to 30% decrease from baseline of the sum of the longest diameters of all target measurable lesions AND absence of any new lesions or unambiguous progression of non-measurable lesions.

Progressive disease: At least a 20% increase in the sum of the LD of target lesions taking as reference the smallest sum LD recorded since the treatment started or the appearance of one or more new lesions Stable disease: neither sufficient shrinkage to qualify for PR nor sufficient increase to qualify for PD, taking as reference the smallest sum LD since treatment started.

Responses for Non-Target Lesion include complete response disappearance of all non-target lesions and normalization of tumor marker level, incomplete response/stable disease: persistence of one or more non-target lesion(s) or/and maintenance of tumor marker level above normal limits, and progressive disease i.e. appearance of one or more new lesions and/or unequivocal progression of existing non-target lesions Toxicity Patients will be queried at each visit regarding: local reactions to vaccine injections; allergic symptoms such as rhinitis, skin rash or itching Performance status, ECOG and Karnofsky; intercurrent infections; changes in medications (especially pain medications); subjective sense of well-being or lack thereof; toxicity will be characterized and graded according to the new NIH Common Toxicity Criteria, CTC Version 3.0, which may be downloaded from the CTEP homepage, http://ctep.info.nih.gov/.

Unexpected or early death or life-threatening toxicity (such as myocardial infarction, renal failure or thromboembolic disease) will be reported immediately to the project investigator, the St. Vincent Medical Center Institutional Review Board, and to the FDA. Grade IV toxicity of any nature, or any grade III toxicity related to allergy or hypersensitivity, will terminate patient accrual unless and until further review and approval by the FDA of whatever changes in experimental design might be indicated. Grade III toxicity other than hypersensitivity will also cause termination of patient accrual if occurring in >1 patient during the first 3 patients or >30% of patients during the course of the study. Grade III toxicity, autoimmune disease, or Grade II hypersensitivity toxicity will preclude further inoculations to the particular patient.

Number of Subjects

The optimal two-stage design of Simon was used to determine sample size and early termination criteria related to vaccine activity[11, 12]. This design minimizes the number of patients treated with a treatment of possible low activity. Assuming a baseline level of response however defined (e.g. clinical, immunological, etc.) of no more than 5% and a response rate of interest of 25%, a false-positive rate (alpha error) of 0.10 and a false-negative rate of 0.10 (power of 0.90), this design calls for 9 patients in a first stage and a maximum of 24 patients. In the first stage, 9 assessable patients are entered and treated. If no responses are observed, the trial is terminated and the regimen is declared inactive. Otherwise, accrual continues to a total of 24 assessable patients. If the total number of clinical responses is at least 3, the regimen is considered clinically active. With this design, the probability of early termination based on activity/response is 0.63 when the true response level is no greater than 5%. This design, with target response rate of 25% and baseline rate of 5%, is considered by Simon, et al. to be "reasonable for many initial vaccine trials" (p. 1850).

Response Definitions

Both objective tumor response (CR or PR) and immunological response will be considered as evidence of activity. Criteria for clinical response have been described in detail in the discussion of RECIST criteria. Three tests will be used for evaluation of vaccine-specific immunological response. Serum antibody levels against live vaccine cells will be measured by cell suspension ELISA. T-cell mediated response will be measured by delayed type hypersensitivity (DTH) skin test and by flow cytometry. The latter test is designed to calculate the frequency of peripheral blood T cells producing interferon-gamma in response to stimulation with monocytes pulsed with vaccine cell lysate. For cell suspension ELISA and flow cytometry assay, a two-fold increase from pre-vaccine to post-vaccine level is considered evidence of response[45]. For DTH, an induration of >5 mm in diameter is commonly considered evidence of reaction[46], although erythema has been considered informative in one recent report[43]. If a patient has either a clinical response or an immunological response on any of the three measures, he/she will be considered to have a biological response. Note that for purposes of publication, only clinical responses of CR or PR will merit designation of "response".

These criteria for response (as well as an alpha error rate of 0.10) are being used because this is an early trial of a new vaccine regimen that is expected to be well tolerated and is being used in patients who have failed the standard therapeutic approaches. Their survival time is expected to be limited under any circumstances, and it is important not to miss a possibly active treatment regimen. Insofar as the patients for this regimen will have very advanced cancer, the absence of toxicity will be considered very significant and will encourage consultation with the FDA for advice for planning further investigations in patients with more favorable prognoses and more robust immune capabilities, Also, early termination can occur based on toxicity, as described earlier in the toxicity section.

Data Analysis

The primary endpoint is toxicity, which does not require statistical analysis, nor does the decision to expand the patient cohort from 9 patients to 24. However, for scientific data review, data will be entered onto CRFs and from there into a computer database (Microsoft Access) for statistical analysis (using SPSS 11.5) if enough patients are accrued to warrant such analysis.

In addition to those variables specifically mentioned in this protocol, which are related to the current treatment and assessments, information on a variety of patient characteristics will also be entered, including but not limited to demographics (age, sex, race/ethnicity), medical history (prior cancer treatments, time interval since previous treatment, sites of disease, etc.), physical exam characteristics, Her2/neu status, and date of death for computing survival time from first vaccine. A variety of statistical analyses will be performed to assess the relationship between clinical response, immunological response, and possible prognostic factors. A chi-square analysis will be used to determine whether any of the three immunological measures are significantly related to clinical response. Multiple regression and/or Cox regression will be performed to identify factors predictive of response if the number of subjects entered into the study so permits. This may include logistic regression when using response as the endpoint and Cox regression when using survival time. Other parametric and nonparametric tests will be used as appropriate to evaluate relationships of interest. For all tests, criterion for statistical significance will be set at $p \leq 0.05$, two-tailed test, as defined above.

REFERENCES

1. Dranoff G. GM-CSF-secreting melanoma vaccines. Oncogene. 2003; 22:3188-92.
2. Fagerberg J. Granulocyte-macrophage-colony-stimulating factor as adjuvant in tumor immunotherapy. Medical Oncology 1996; 13:155-160.
3. Jaffee E M, Hruban R H, Biedrzycki B, et al. Novel allogeneic granulocyte-macrophage colony-stimulating factor-secreting tumor vaccine for pancreatic cancer: a phase I trial of safety and immune activation. Journal of Clinical Oncology. 2001; 19:145-56.
4. Ribas A B L, Glaspy J A, Economou J S. Cancer immunotherapy using gene-modified dendritic cells. Current Gene Therapy 2002; 2:57-78.
5. Proietti E G G, Garrone B, et al. Importance of cyclophosphamide induced bystander effect on T cells for a successful tumor eradication in response to adoptive immunotherapy in mice. J Clin Invest 1998; 101:429-41.
6. Chen W. Novel cancer vaccines. Expert Opin. Ther. Patents 2001; 11:937-950.
7. Berd D M J H, Mastrangelo M. Induction of cell-mediated immunity to autoloogus melanoma cells and regression of metastases after treatment with a melanoma cell vaccine preceded by cyclophosphamide. Cancer Research 1986; 46:2572-77.
8. Kuroi K, Sato Y, Yamaguchi Y, Toge T. Modulation of suppressor cell activities by cyclophosphamide in breast cancer patients. Journal of Clinical Laboratory Analysis. 1994; 8:123-7.
9. Proietti E, Bracci L, Puzelli S, et al. Type I IFN as a Natural Adjuvant for a Protective Immune Response: Lessons from the Influenza Vaccine Model. J Immunol 2002; 169:375-383.
10. Santini S M, Lapenta C, Logozzi M, et al. Type I interferon as a powerful adjuvant for monocyte-derived dendritic cell development and activity in vitro and in Hu-PBL-SCID mice. Journal of Experimental Medicine. 2000; 191:1777-88.
11. Simon R M S S, Hamilton M, et al. Clinical trial designs for the early clinical development of therapeutic cancer vaccines. J Clin Oncol 2001; 19:1848-1854.
12. Simon ROt-sdfpIctCCT, 1989, 10:1-10, Optimal two-stage designs for phase II clinical trials. Clinical Trials, 1989, 10:1-10, 1989; 10:1-10.
13. Fossati R CC, Torri V, et al. Cytotoxic and hormonal treatment for metastatic breast cancer: a systematic review of published randomized trials involving 31, 510 women. J Clin Oncol 1998; 16:3439-346.
14. Greenberg P A HG, Smith T L et alq. Long-term follow-up of patients with complete remission following combination chemotherapy for metastatic brest cancer. J Clin Oncol 1996; 16:2197-05.
15. Hortobagyi G N, Gutterman J U, Blumenschein G R, et al. Immunotherapy and chemo-immunotherapy of human breast cancer. Immunotherapy of Human Cancer. New York: Raven Press, 1978:321-345.
16. Hadden J W. The immunology and immunotherapy of breast cancer: an update. International Journal of Immunopharmacology. 1999; 21:79-101.
17. Renkvist N. C C, Robbin P F, Parmiani G. A listing of human tumor antigens recognized by T cells. Cancer Immunology Immunotherapy 2001; 50:3-16.
18. Wiseman C, Cailleau R, Olive M, Blumenschein G R, Bowen J M. Autologous and homologous immunofluorescent antibody to established breast cancer cell lines. In Vitro 1980; 16:629-33.
19. Wiseman C L, Bowen J M, Hersh E M. Human immune response to mouse mammary tumor virus (MMTV), Proc Amer Assoc Cancer Res, 1979. Vol. 20.
20. Wiseman C L, Bowen J M, Davis J W, Hersh E M, Brown B W, Blumenschein G R. Human lymphocyte blastogenesis responses to mouse mammary tumor virus. J Natl Cancer Inst 1980; 64:425-30.
21. An Y W, Peliss I, Melana S M, Go V, Holland J F, Pogo B G. MMTV-like env gene sequences in human breast cancer. Archives of Virology. 2001; 146:171-80.
22. Springer G F. T and Tn pancarcinoma markers: autoantigenic adhesion molecules in pathogenesis, prebiopsy car- 23. Holmberg L A B S. Theratope vaccine (STn-KLH). Expert Opin. Biol. Ther 2001; 1:881-91.
24. Wolchok J D, PB aC. How can we tell when cancer vaccines vaccinate. J Clin Oncol 2003; 21:586-7.
25. Lyerly H K M M, Clay T M. Surrogate markers of effective anti-tumor immunity. J Surg Onc 2001; 8:190-1.
26. Jiang X P, Yang D C, Elliott R L, Head J F. Vaccination with a mixed vaccine of autogenous and allogeneic breast cancer cells and tumor associated antigens CA15-3, CEA and CA125—results in immune and clinical responses in breast cancer patients. Cancer Biotherapy & Radiopharmaceuticals. 2000; 15:495-505.
27. Krause S W N C, Soruri A, Mayers S, Peters J H, Andreesen R. The treatment of patients with disseminated malignant melanoma by vaccination with autologous cell hybrids of tumor cells and denddritic cells. J Immunohter 2002; 25:421-8.
28. Peters J H. Therapeutic tumor vaccination with autologous dendritic cells. LTBH Medical Research Institute Cutting Edge Seminar May 30, 2003 2003.
29. MacLean G D, Miles D W, Rubens R D, Reddish M A, Longenecker B M. Enhancing the effect of THERATOPE STn-KLH cancer vaccine in patients with metastatic breast cancer by pretreatment with low-dose intravenous cyclophosphamide. Journal of Immunotherapy with Emphasis on Tumor Immunology. 1996; 19:309-16.
30. Disis M. L. G K, Lleath P R et al. Therapeutic vaccines: targetting the Future of Cancer Treatment: Medsacpe, 2002.
31. Nemunaitis J, Sterman D, Jablons D, et al. Granulocyte-Macrophage Colony-Stimulating Factor Gene-Modified Autologous Tumor Vaccines in Non-Small-Cell Lung Cancer. J Natl Cancer Inst 2004; 96:326-331.
32. Couch M, Saunders J K, O'Malley B W, Jr., Pardoll D, Jaffee E. Spatial distribution of tumor vaccine improves efficacy. Laryngoscope. 2003; 113:1401-5.
33. Szollosi J, Balazs, M., Feuerstein, B. G., Benz, C. C., Waldman, F. M. ERBB-2 (HER2/neu) gene copy number, p185HER2 overexpression, and intratumor heterogeneity in human breast cancer. Cancer Res. 1995; 55:5400-7.
34. Greten T F, Jaffee E M. Cancer vaccines. Journal of Clinical Oncology. 1999; 17:1047-60.
35. Wiseman C, Hood Y, Presant C, Kennedy P. OKT-3/cyclophosphamide up-regulation of peripheral blood killer-lymphocyte subsets in human cancer patients. Mol Biother 1991; 3:63-7.
36. Schiavoni G, Mattei F, Di Pucchio T, et al. Cyclophosphamide induces type I interferon and augments the number of CD44hi T lymphocytes in mice: implications for strategies of chemoimmunotherapy of cancer. Blood 2000; 95:2024-2030.
37. Boyer C M, Dawson D V, Neal S E, et al. Differential induction by interferons of major histocompatibility complex-encoded and non-major histocompatibility complex-encoded antigens in human breast and ovarian carcinoma cell lines. Cancer Research. 1989; 49:2928-34.
38. Machiels J P, Reilly R T, Emens L A, et al. Cyclophosphamide, doxorubicin, and paclitaxel enhance the antitumor immune response of granulocyte/macrophage-colony stimulating factor-secreting whole-cell vaccines in HER2/neu tolerized mice. Cancer Research. 2001; 61:3689-97.
39. Kharazi A ea. Rhodes. 2003.
40. Paquette R, Hsu N, Kiertscher S, et al. Interferon-alpha and granulocyte-macrophage colony-stimulating factor differentiate peripheral blood monocytes into potent antigen-presenting cells. J Leukoc Biol 1998; 64:358-367.
41. Findler M, Cantor J, Haddad L, Gordon W, Ashman T. The reliability and validity of the SF-36 health survey questionnaire for use with individuals with traumatic brain injury. Brain Injury. 2001; 15:715-23.
42. Disis M. L. G K, Lleath P R et al. Generation of immunity to the Her2/neu oncogenic protein in patients with breast and ovarian cancer using a peptide-based vaccine. Clin Cancer Res 1999; 5:1289-97.
43. Lotern M PT, Driza O, Weitzen R, et al Shiloni E. Autologous cell vaccine as a post-operative adjuvant treatment for high-risk1 melanoma patients (AJCC Stages III and IV). Brit J Cancer 2002; 86:1534-39.
44. Therasse P, Arbuck S G, Eisenhauer E A, et al. New Guidelines to Evaluate the Response to Treatment in Solid Tumors. J Natl Cancer Inst 2000; 92:205-216.
45. Kammula U S M F, Rosenberg S A. Real-time quantitative polymerase chain reaction assessment of immune reactivity in melanoma patients after tumor peptie vaccination. JNCI 2000; 92:1336-44.
46. Baars A, Claessen A M E, van den Eertwegh A J M, et al. Skin tests predict survival after autologous tumor cell vaccination in metastatic melanoma: Experience in 81 patients. [Article]. Annals of Oncology August 2000; 11:965-970.

We claim:

1. A composition comprising at least one SV-BR cell having each of the following characteristics:
   (a) grows as an epithelial, adherent monolayer culture;
   (b) does not overexpress estrogen receptors;
   (c) overexpresses her2/neu;
   (d) is sensitive in vitro to cyclophosphamide (4HC);
   (e) is sensitive in vitro to etoposide;
   (f) is sensitive in vitro to taxol;
   (g) is resistant in vitro to carboplatin;
   (h) demonstrates karyotypic abnormalities;
   (i) is aneuploid cell; and a physiologically acceptable carrier.

2. The composition of claim 1, wherein the SV-BR cell is an SV-BR-1 cell, deposited as American Type Culture Collection Accession No. PTA-7812.

3. The composition of claim 1, wherein the SV-BR cell is an SV-BR-1-GM cell, deposited as American Type Culture Collection Accession No. PTA-7813.

4. The composition of claim 1, wherein the SV-BR cell is selected from the group consisting of breast cancer cell, ovarian cancer cell and lung cancer cell.

5. A composition for inducing an immune response in a subject in need thereof, comprising a physiologically acceptable carrier and at least one SV-BR cell, an SV-BR cell having each of the following characteristics:
   (a) grows as an epithelial, adherent monolayer culture;
   (b) does not overexpress estrogen receptors;
   (c) overexpresses her2/neu;
   (d) is sensitive in vitro to cyclophosphamide (4HC);
   (e) is sensitive in vitro to etoposide;
   (f) is sensitive in vitro to taxol;
   (g) is resistant in vitro to carboplatin;
   (h) demonstrates one or more of the following karyotypic abnormalities: 57-60, XX+1, add(1)(36.3), del (1)add(1)(p36.3)add(1)(q32), i(3)(q10), add(4)(p16), +6, −10, −10, +11, +12, −14, +15, +16, add(19)(q13.4), +20, −21, −21, +11, −13mar[cp20]; and (i) is aneuploid cell.

6. The composition of claim 5, wherein the SV-BR cell is an SV-BR-1 cell, deposited as American Type Culture Collection Accession No. PTA-7812.

7. The composition of claim 5, wherein the SV-BR cell is an SV-BR-1-GM cell, deposited as American Type Culture Collection Accession No. PTA-7813.

8. The composition of claim 5, wherein the SV-BR cell is selected from the group consisting of breast cancer cell, ovarian cancer cell and lung cancer cell.

9. The composition of claim 5, further comprising a cytokine.

10. The composition of claim 9, wherein the cytokine is selected from the group consisting of LFN-α, IL-2, IL-4, IL-12 and GM-CSF.

11. The composition of claim 5, wherein the cell is genetically modified to express at least one polypeptide selected from the group consisting of a chemokine, a cytokine, a growth factor, a tumor antigen or an antibody.

12. The composition of the claim 11, wherein the cytokine is GM-CSF, IL-2, IL-4, IL-12 or IFN-α.

13. The composition of claim 11, wherein the growth factor is an Flt3L polypeptide.

14. The composition of claim 11, wherein the tumor antigen selected from the group consisting of HER2/neu, CA 15.3, CD31, CD105 Tie-2Tek, NY-ESO-1 MTA1, MUC1, (CEA), Ep-CAM, p53, MAGE 1, 2, 3, 4, 6 or 12, and Thompson-Friedenreich antigen.

15. The composition of claim 11, wherein the antibody comprises a monoclonal antibody.

16. The composition of claim 11, wherein the antibody is a humanized antibody, a single chain antibody or a chimeric antibody.

17. The composition of claim 11, wherein the antibody is specific for a cancer antigen.

18. The composition of claim 17, wherein the cancer antigen is a breast cancer antigen.

19. The composition of claim 5, wherein the subject is afflicted with a tumor or with cancer.

20. The composition of claim 19, wherein the cancer is breast cancer.

21. The composition of claim 20, wherein the breast cancer comprises a ductal hyperplasia, a carcinoma in situ, an invasive ductal carcinoma, a medullary carcinoma, or a combination thereof.

22. The composition of claim 5, further comprising a cell of a second type.

23. The composition of claim 22, wherein the cell of the second type is a lymphocyte or a tumor cell.

24. A method of inducing an immune response in a subject in need thereof, comprising administering to the subject a therapeutically effective amount of the composition of claim 5.

25. The method of claim 24, wherein the SV-BR cells are SV-BR-1 cells, deposited as American Type Culture Collection Accession No. PTA-7812.

26. The method of claim 24, wherein the SV-BR cells are SV-BR-1-GM cells, deposited as American Type Culture Collection Accession No. PTA-7813.

27. The method of claim 24, wherein the SV-BR cells are selected from the group consisting of breast cancer cells, ovarian cancer cells and lung cancer cells.

28. A method of treating a tumor or a cancer in a subject in need thereof, comprising administering to the subject a therapeutically effective amount of the composition of claim 5.

29. The method of claim 28, wherein the SV-BR cells are SV-BR-1 cells, deposited as American Type Culture Collection Accession No. PTA-7812.

30. The method of claim 28, wherein the SV-BR cells are SV-BR-1-GM cells, deposited as American Type Culture Collection Accession No. PTA-7813.

31. The method of claim 28, wherein the SV-BR cells are selected from the group consisting of breast cancer cells, ovarian cancer cells and lung cancer cells.

32. The method of claim 28, wherein the subject is afflicted with a tumor or with cancer.

33. The method of claim 28, wherein the cancer is a breast cancer.

34. The method of claim 33, wherein the breast cancer is a stage 0, I, II, III or IV stage breast cancer.

35. The method of claim 34, wherein the breast cancer comprises a ductal carcinoma or a lobular carcinoma.

36. The method of claim 28, wherein the tumor overexpresses her2 or EGFR or both.

37. The method of claim 28, wherein the cancer is an ovarian or lung cancer.

38. The method of claim 28, wherein the composition is administered to the subject at least twice.

39. The method of claim 28, wherein the composition comprises at least one adjuvant.

40. The method of claim 28, further comprising treating the subject with surgery, chemotherapy, radiation therapy, hormonal therapy, biological therapy, or a combination thereof.

* * * * *

UNITED STATES PATENT AND TRADEMARK OFFICE
CERTIFICATE OF CORRECTION

PATENT NO.         : 7,674,456 B2                                                   Page 1 of 1
APPLICATION NO.    : 10/868094
DATED              : March 9, 2010
INVENTOR(S)        : Wiseman et al.

It is certified that error appears in the above-identified patent and that said Letters Patent is hereby corrected as shown below:

In the abstract, line 3, delete "PTA-1712" insert --PTA-7812--; line 4, delete "PTA-1713" insert --PTA-7813--.

Column 1, line 61, delete "PTA-1712" insert --PTA-7812--; line 62, delete "PTA-1713" insert --PTA-7813--.

Column 3, line 7, delete "PTA-1712" insert --PTA-7812--; line 10, delete "PTA-1713" insert --PTA-7813--; line 18, delete "PTA-1712" insert --PTA-7812--; line 23, delete "PTA-1713" insert --PTA-7813--; line 51, delete "PTA-1713" insert --PTA-7813--.

Signed and Sealed this

First Day of June, 2010

David J. Kappos
*Director of the United States Patent and Trademark Office*